US010597418B2

(12) United States Patent
Mao et al.

(10) Patent No.: US 10,597,418 B2
(45) Date of Patent: *Mar. 24, 2020

(54) NON-CALORIC SWEETENER

(71) Applicant: Conagen Inc., Bedford, MA (US)

(72) Inventors: Guohong Mao, Burlington, MA (US); Venkata Sai Prakash Chaturvedula, Mission Viejo, CA (US); Xiaodan Yu, Lexington, MA (US)

(73) Assignee: Conagen Inc., Bedford, MA (US)

( * ) Notice: Subject to any disclaimer, the term of this patent is extended or adjusted under 35 U.S.C. 154(b) by 58 days.

This patent is subject to a terminal disclaimer.

(21) Appl. No.: 15/701,599

(22) Filed: Sep. 12, 2017

(65) Prior Publication Data
US 2018/0009835 A1    Jan. 11, 2018

Related U.S. Application Data

(60) Continuation of application No. 15/016,750, filed on Feb. 5, 2016, now Pat. No. 10,138,263, which is a division of application No. 14/269,435, filed on May 5, 2014, now Pat. No. 9,522,929.

(51) Int. Cl.
C07H 15/24      (2006.01)
C07H 15/256     (2006.01)
C12N 9/10       (2006.01)
C12P 19/56      (2006.01)

(52) U.S. Cl.
CPC .......... C07H 15/24 (2013.01); C07H 15/256 (2013.01); C12N 9/10 (2013.01); C12N 9/1048 (2013.01); C12N 9/1051 (2013.01); C12N 9/1062 (2013.01); C12P 19/56 (2013.01); C07K 2319/00 (2013.01); C12Y 204/01013 (2013.01); C12Y 204/01017 (2013.01)

(58) Field of Classification Search
None
See application file for complete search history.

(56) References Cited

U.S. PATENT DOCUMENTS

| | | | |
|---|---|---|---|
| 9,107,436 B2 | 8/2015 | Purkayastha et al. |
| 9,522,929 B2 | 12/2016 | Mao et al. |
| 9,527,880 B2 | 12/2016 | Mao et al. |
| 9,567,619 B2 | 2/2017 | Mao et al. |
| 9,643,990 B2 | 5/2017 | Mao et al. |
| 9,765,104 B2 | 9/2017 | Mao et al. |
| 9,783,566 B2 | 10/2017 | Mao et al. |
| 9,850,270 B2 | 12/2017 | Mao et al. |
| 9,988,414 B2 | 6/2018 | Mao et al. |
| 10,138,263 B2 | 11/2018 | Mao et al. |
| 2008/0148432 A1 | 6/2008 | Abad |
| 2009/0183270 A1 | 7/2009 | Adams et al. |
| 2014/0329281 A1 | 11/2014 | Houghton-Larson et al. |
| 2014/0357588 A1 | 12/2014 | Markosyan et al. |
| 2015/0315623 A1 | 11/2015 | Mao et al. |
| 2016/0095338 A1 | 4/2016 | Mao et al. |
| 2016/0097070 A1 | 4/2016 | Mao et al. |
| 2016/0097071 A1 | 4/2016 | Mao et al. |
| 2016/0097072 A1 | 4/2016 | Mao et al. |
| 2016/0153018 A1 | 6/2016 | Mao et al. |
| 2016/0207954 A1 | 7/2016 | Mao et al. |
| 2016/0208225 A1 | 7/2016 | Mao et al. |
| 2016/0208303 A1 | 7/2016 | Mao et al. |
| 2016/0298159 A1 | 10/2016 | Tao et al. |
| 2017/0181452 A1 | 6/2017 | Mao et al. |
| 2017/0196248 A1 | 7/2017 | Mao et al. |
| 2017/0218420 A1 | 8/2017 | Mao et al. |
| 2017/0218421 A1 | 8/2017 | Mao et al. |
| 2017/0362267 A1 | 12/2017 | Mao et al. |
| 2018/0037600 A1 | 2/2018 | Mao et al. |
| 2018/0051049 A1 | 2/2018 | Mao et al. |
| 2018/0080055 A1 | 3/2018 | Mao et al. |
| 2018/0244709 A1 | 8/2018 | Mao et al. |

FOREIGN PATENT DOCUMENTS

| | | |
|---|---|---|
| CN | 102559528 A | 7/2012 |
| CN | 102766667 A | 11/2012 |
| CN | 103397064 A | 11/2013 |
| CN | 104232496 A | 12/2014 |
| JP | H4-149191 A | 5/1992 |
| WO | WO 2002/010210 | 2/2002 |
| WO | WO 2011/028671 | 3/2011 |
| WO | WO 2011/097620 A1 | 8/2011 |
| WO | WO 2012/125991 | 9/2012 |
| WO | WO 2013/022989 | 2/2013 |
| WO | WO 2013/093880 | 6/2013 |
| WO | WO 2013/093881 | 6/2013 |
| WO | WO 2013/096290 | 6/2013 |
| WO | WO 2013/096663 | 6/2013 |
| WO | WO 2013/110673 | 8/2013 |

(Continued)

OTHER PUBLICATIONS

Third Party Submission Under 37 CFR §1.290 for U.S. Appl. No. 15/016,750, filed Feb. 7, 2017.
Third Party Submission Under 37 CFR §1.290 for U.S. Appl. No. 15/701,613, filed Aug. 8, 2018.
Amendment and Response to Non-final Office Action for U.S. Appl. No. 14/269,435 dated Jul. 7, 2016.
Bock, The UDP-glycosyltransferase (UGT) superfamily expressed in humans, insects and plants: Animal-plant arms-race and co-evolution. Biochem Pharmacol.Jan. 1, 2016;99:11-7. doi: 10.1016/j.bcp.2015.10.001. Epub Oct. 8, 2015.

(Continued)

Primary Examiner — Suzanne M Noakes
(74) Attorney, Agent, or Firm — Wolf, Greenfield & Sacks, P.C.; Karen K. Chan

(57) ABSTRACT

Disclosed is a steviol glycoside referred to as rebaudioside D2. Rebaudioside D2 has five β-D-glucosyl units connected to the aglycone steviol. Also disclosed are methods for producing rebaudioside D2, a UDP-glycosyltransferase fusion enzyme, and methods for producing rebaudioside D and rebaudioside E.

10 Claims, 13 Drawing Sheets
Specification includes a Sequence Listing.

(56) References Cited

FOREIGN PATENT DOCUMENTS

| WO | WO 2013/176738 | 11/2013 |
| --- | --- | --- |
| WO | WO 2014/122227 | 8/2014 |
| WO | WO 2014/193934 A1 | 12/2014 |
| WO | WO 2015/065650 A2 | 5/2015 |
| WO | WO 2015/171555 | 11/2015 |
| WO | WO 2016/054534 A1 | 4/2016 |

OTHER PUBLICATIONS

Elleuche, Bringing functions together with fusion enzymes—from nature's inventions to biotechnological applications. Appl Microbiol Biotechnol. Feb. 2015;99(4):1545-56. doi: 10.1007/s00253-014-6315-1. Epub Dec. 24, 2014.

Son et al., Production of flavonoid o-glucoside using sucrose synthase and flavonoid o-glucosyltransferase fusion protein. J Microbiol Biotechnol. Jul. 2009;19(7):709-12.

UniprotKB accession No. B8AQD6_ORYSI. Mar. 3, 2009. Yu et al.

UniprotKB accession No. P49040. Feb. 1, 1996. Martin et al.

Zheng et al., The structure of sucrose synthase-1 from *Arabidopsis thaliana* and its functional implications. J Biol Chem. Oct. 14, 2011;286(41):36108-18. doi: 10.1074/jbc.M111.275974. Epub Aug. 24, 2011.

Bieniawska et al., Analysis of the sucrose synthase gene family in *Arabidopsis*. Plant J. Mar. 2007;49(5):810-28.

Chaturvedula et al., NMR Spectral Analysis And Hyrdolysis Studies Of Rebaudioside N, A Minor Steviol Glycoside Of Stevia Rebaudiana Bertoni. Food and Nutrition Science. Oct. 2013; 4(10):1004-8.

Hong et al., A cell plate-specific callose synthase and its interaction with phragmoplastin. Plant Cell. Apr. 2001;13(4):755-68.

Kim et al., Natural high potency sweeteners. Handbook of Sweeteners. S. Marie et al. (eds.). Springer Science +Business Media. New York. 1991;116-185.

Kraska et al., GRAS Assessment of Glucosylated Steviol Glycosides STEVITEN RICH Food Usage Conditions for General Recognition of Safety for DAEPYUNG Co., Ltd. GRAS Notice (GRN) No. 448; Sep. 27, 2012; 63 pages.

Kubica et al., Determination of eight artificial sweeteners and common Stevia rebaudiana glycosides in non-alcoholic and alcoholic beverages by reversed-phase liquid chromatography coupled with tandem mass spectrometry. Anal Bioanal Chem. Feb. 2015;407(5):1505-12. doi: 10.1007/s00216-014-8355-x. Epub Dec. 4, 2014.

Martin et al., Expression of an *Arabidopsis* sucrose synthase gene indicates a role in metabolization of sucrose both during phloem loading and in sink organs. Plant J. Aug. 1993;4(2):367-77.

Masada et al., An efficient chemoenzymatic production of small molecule glucosides with in situ UDP-glucose recycling. FEBS Lett. May 29, 2007;581(13):2562-6.

Prakash et al., Bioconversion of rebaudioside I from rebaudioside A. Molecules. Oct. 28, 2014;19(11):17345-55. doi: 10.3390/molecules191117345.

Prakash et al., Catalytic hydrogenation of the sweet principles of Stevia rebaudiana, Rebaudioside B, Rebaudioside C, and Rebaudioside D and sensory evaluation of their reduced derivatives. Int J Mol Sci. Nov. 16, 2012;13(11):15126-36. doi: 10.3390/ijms131115126.

Prakash et al., Isolation and characterization of a novel rebaudioside M isomer from a bioconversion reaction of rebaudioside A and NMR comparison studies of rebaudioside M isolated from Stevia rebaudiana Bertoni and Stevia rebaudiana Morita. Biomolecules. Mar. 31, 2014;4(2):374-89. doi: 10.3390/biom4020374.

Prakash et al., Isolation and structure elucidation of rebaudioside D2 from bioconversion reaction of rebaudioside A to rebaudioside D. Nat Prod Commun. Aug. 2014;9(8):1135-8.

Reeck et al., "Homology" in proteins and nucleic acids: a terminology muddle and a way out of it. Cell. Aug. 28, 1987;50(5):667.

Terasaka et al., In situ UDP-glucose regeneration unravels diverse functions of plant secondary product glycosyltransferases. FEBS Lett. Dec. 14, 2012;586(24):4344-50. doi: 10.1016/j.febslet.2012.10.045.

International Search Report and Written Opinion for International Application No. PCT/US2016/027458 dated Sep. 26, 2016.

International Preliminary Report on Patentability for International Application No. PCT/US2016/027458 dated Oct. 27, 2017.

Coleman et al., Up-regulation of sucrose synthase and UDP-glucose pyrophosphorylase impacts plant growth and metabolism. Plant Biotechnol J. Jan. 2006;4(1):87-101.

Uniprot accession No. F2DT21. May 31, 2011.

Zhang et al., Screening for glycosylphosphatidylinositol-modified cell wall proteins in Pichia pastoris and their recombinant expression on the cell surface. Appl Environ Microbiol. Sep. 2013;79(18):5519-26. doi: 10.1128/AEM.00824-13. Epub Jul. 8, 2013.

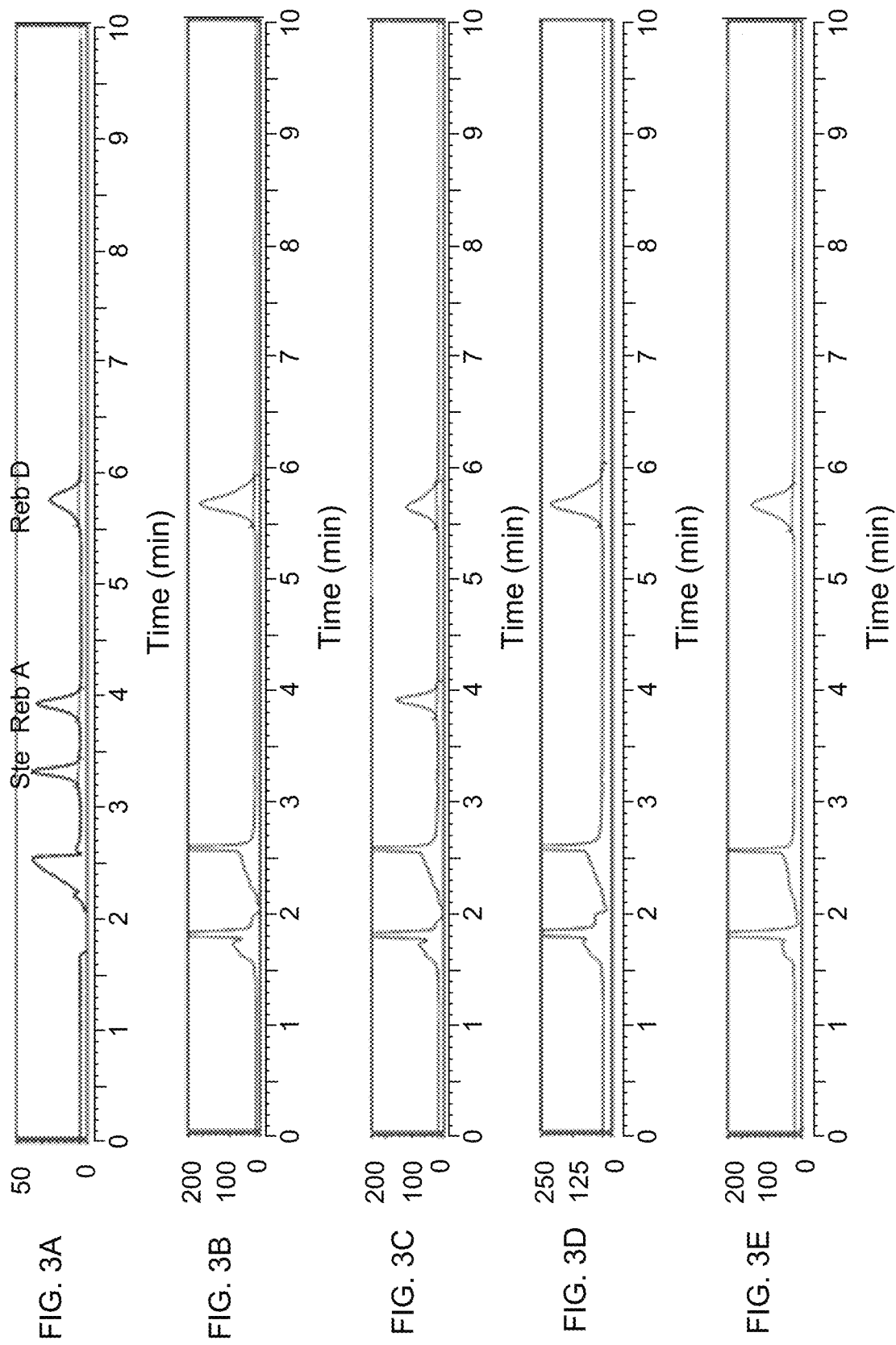

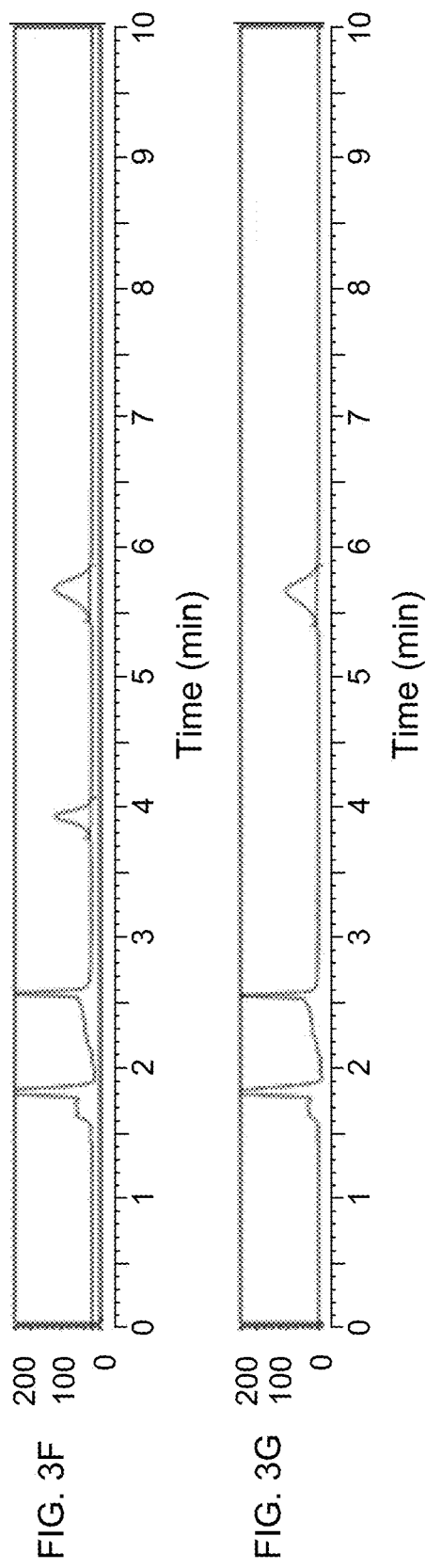

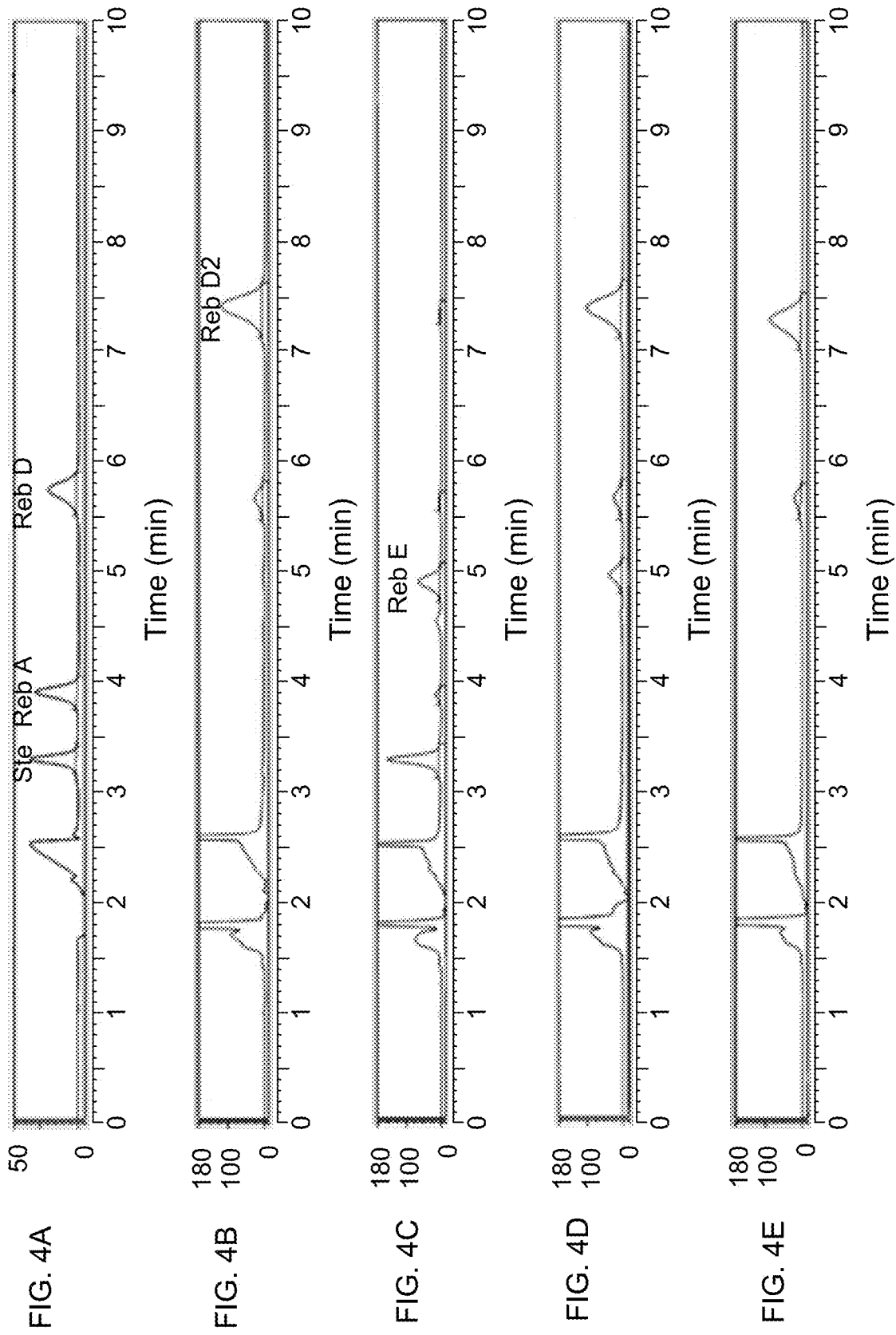

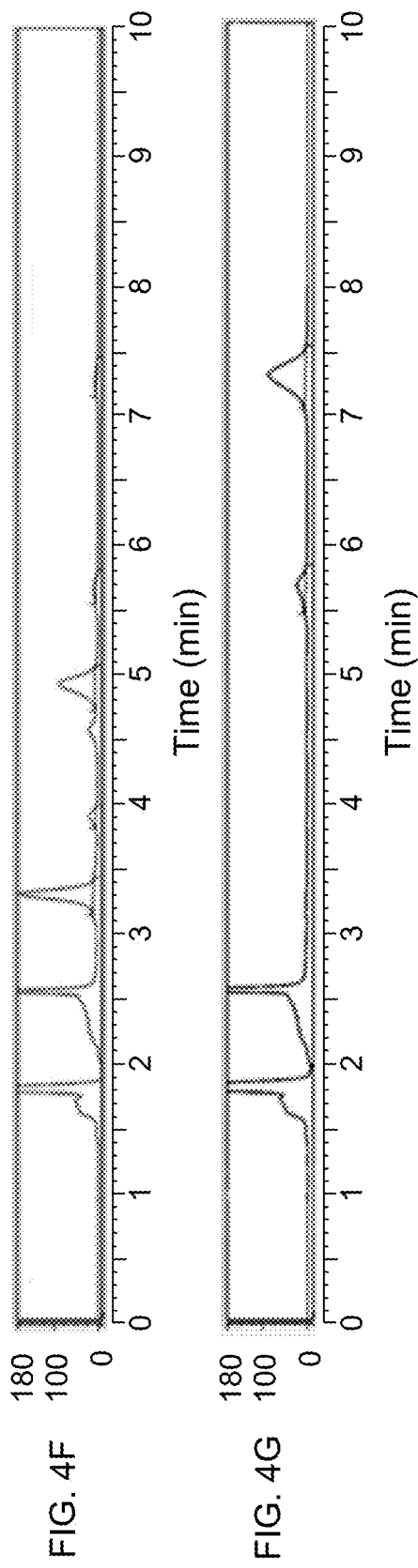

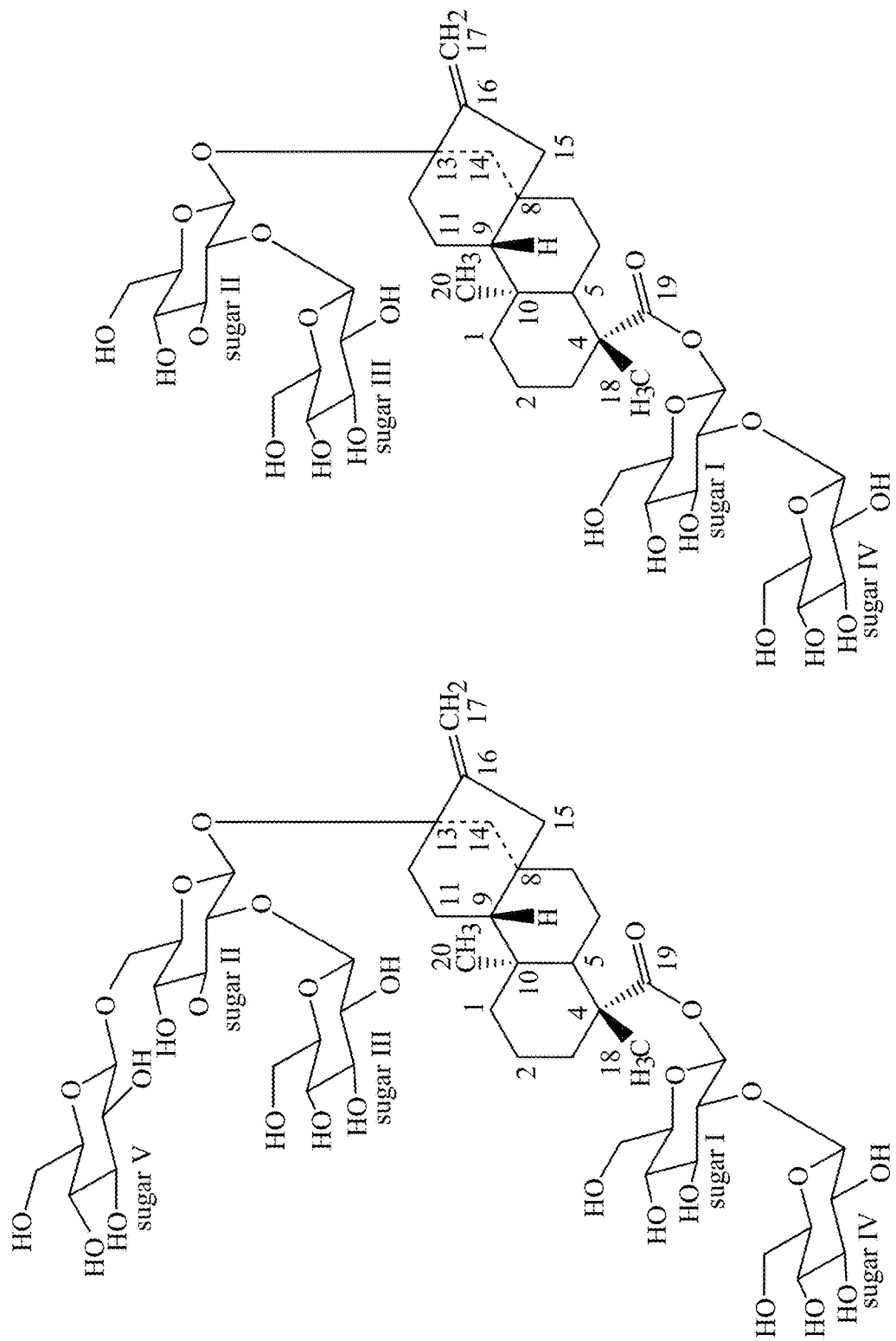
FIG. 6A Rebaudioside D2
FIG. 6B Rebaudioside E

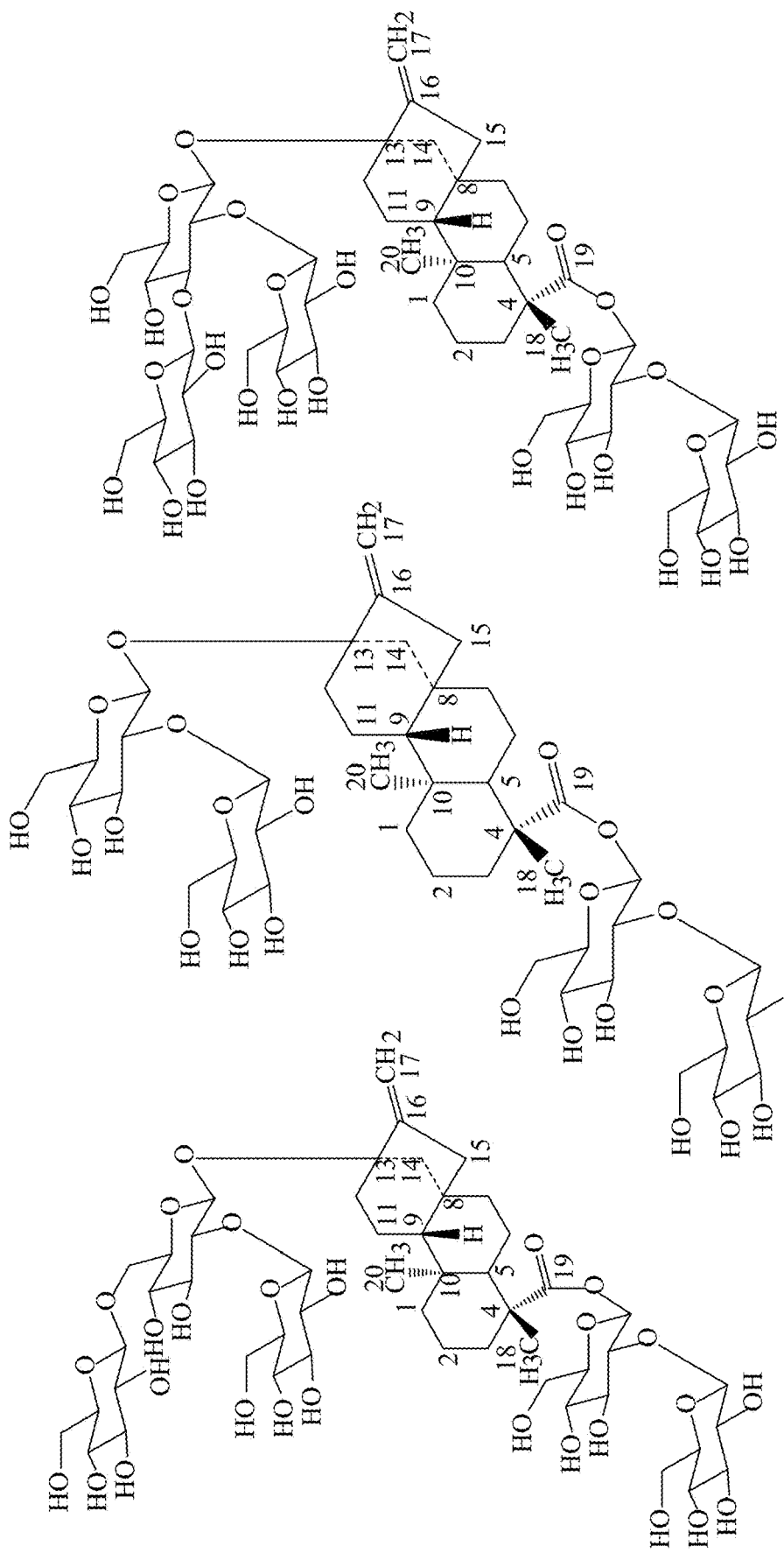
FIG. 8C Rebaudioside D
FIG. 8B Rebaudioside E
FIG. 8A Rebaudioside D2

NON-CALORIC SWEETENER

CROSS-REFERENCE TO RELATED APPLICATIONS

This Application is a continuation of U.S. application Ser. No. 15/016,750, entitled "NON-CALORIC SWEETENER" filed on Feb. 5, 2016, which is a divisional of U.S. application Ser. No. 14/269,435, entitled "NON-CALORIC SWEETENER" filed on May 5, 2014. The entire contents of these applications are incorporated herein by reference in their entirety.

STATEMENT IN SUPPORT FOR FILING A SEQUENCE LISTING

A computer readable form of the Sequence Listing containing the file named "C149770008US04-SEQ-AM.txt", which is 32,681 bytes in size (as measured in MICROSOFT WINDOWS® EXPLORER), is provided herewith and is herein incorporated by reference. This Sequence Listing consists of SEQ ID NOs:1-6.

BACKGROUND OF THE DISCLOSURE

The present disclosure relates generally to natural sweeteners. More particularly, the present disclosure relates to a non-caloric sweetener and methods for synthesizing the non-caloric sweetener.

Steviol glycosides are natural products isolated from *Stevia rebaudiana* leaves. Steviol glycosides are widely used as high intensity, low-calorie sweeteners and are significantly sweeter than sucrose. Naturally occurring steviol glycosides share the same basic steviol structure, but differ in the content of carbohydrate residues (e.g., glucose, rhamnose and xylose residues) at the C13 and C19 positions. Steviol glycosides with known structures include, steviol, stevioside, rebaudioside A, rebaudioside B, rebaudioside C, rebaudioside D, rebaudioside E, rebaudioside F and dulcoside A (see e.g., Table 1).

TABLE 1

| Name | Structure | Molecular Formula | Molecular Weight |
|------|-----------|-------------------|------------------|
| Steviol | 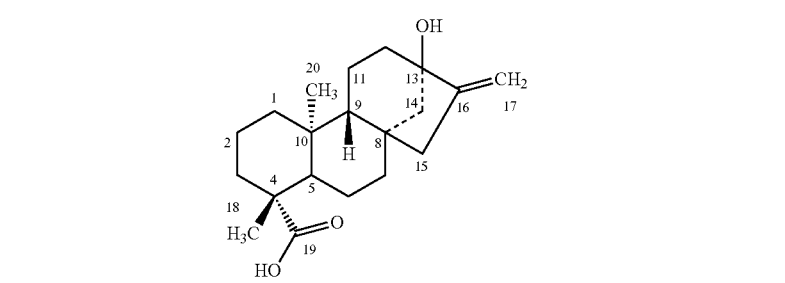 | $C_{20}H_{30}O_3$ | 318 |
| Stevioside | 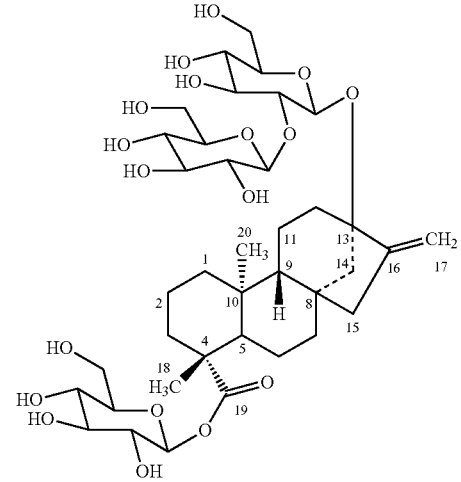 | $C_{38}H_{60}O_{18}$ | 804 |

TABLE 1-continued

Steviol glycosides.

| Name | Structure | Molecular Formula | Molecular Weight |
|---|---|---|---|
| Rebaudioside A | 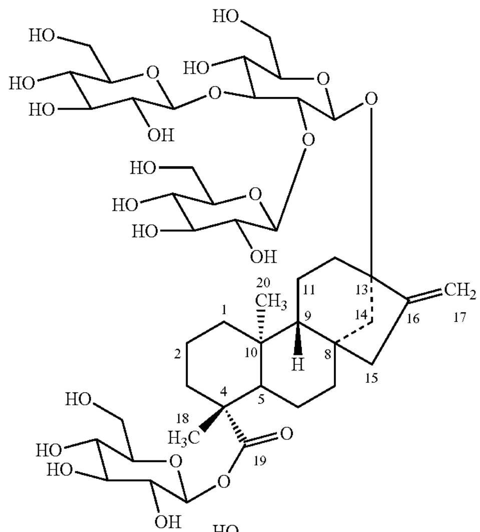 | $C_{44}H_{70}O_{23}$ | 966 |
| Rebaudioside-B | 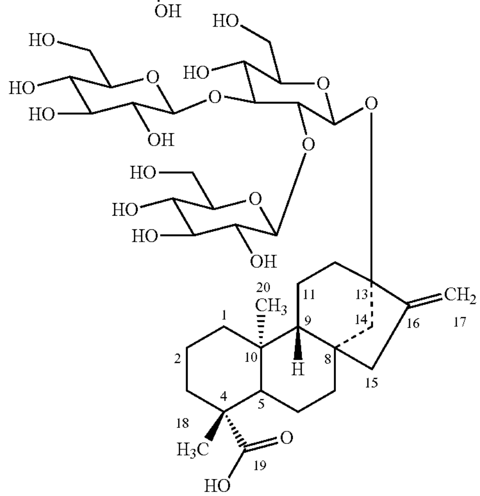 | $C_{38}H_{60}O_{18}$ | 804 |
| Rebaudioside C | 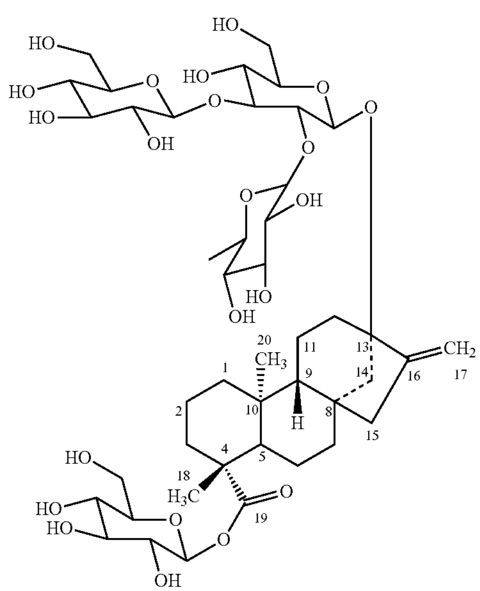 | $C_{44}H_{70}O_{22}$ | 950 |

TABLE 1-continued
Steviol glycosides.
| Name | Structure | Molecular Formula | Molecular Weight |
|---|---|---|---|
| Rebaudioside D | 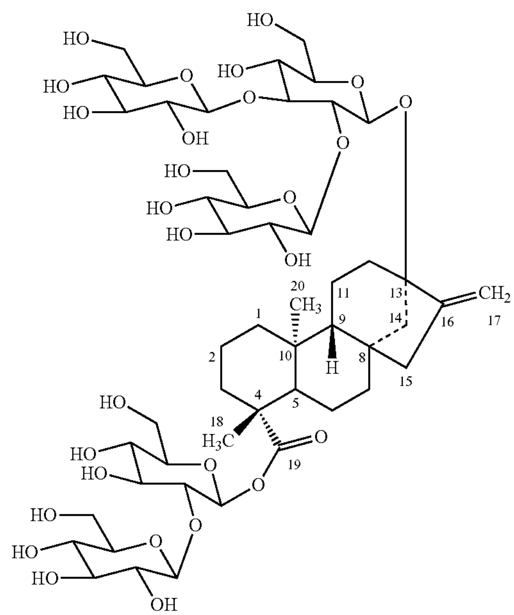 | $C_{50}H_{80}O_{28}$ | 1128 |
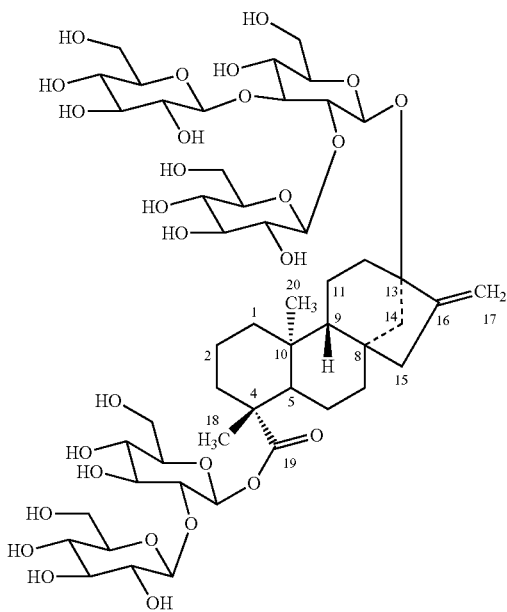
| | | | |
|---|---|---|---|
| Rebaudioside E | | $C_{44}H_{70}O_{23}$ | 966 |
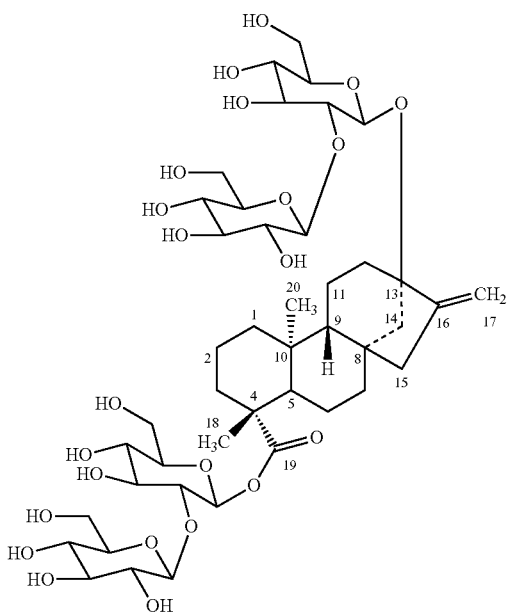

TABLE 1-continued
Steviol glycosides.
| Name | Structure | Molecular Formula | Molecular Weight |
|---|---|---|---|
| Rebaudioside F | 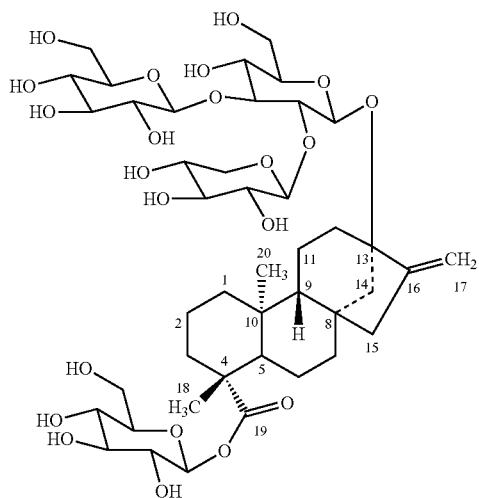 | $C_{43}H_{68}O_{22}$ | 936 |
| Rebaudioside D2 | 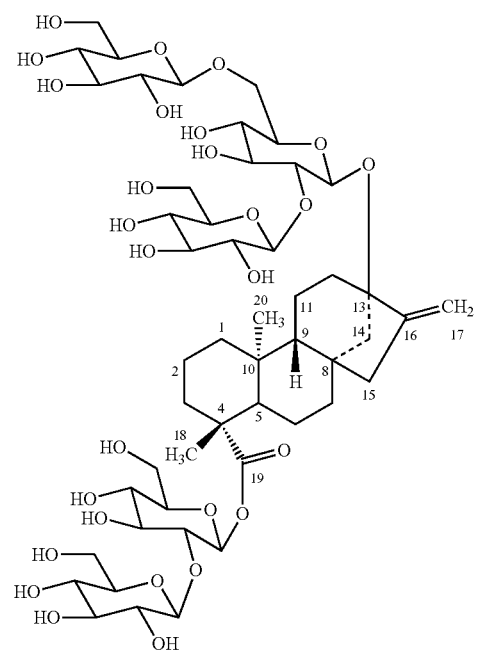 | $C_{50}H_{80}O_{28}$ | 1128 |

TABLE 1-continued

Steviol glycosides.

| Name | Structure | Molecular Formula | Molecular Weight |
|------|-----------|-------------------|------------------|
| Dulcoside A | 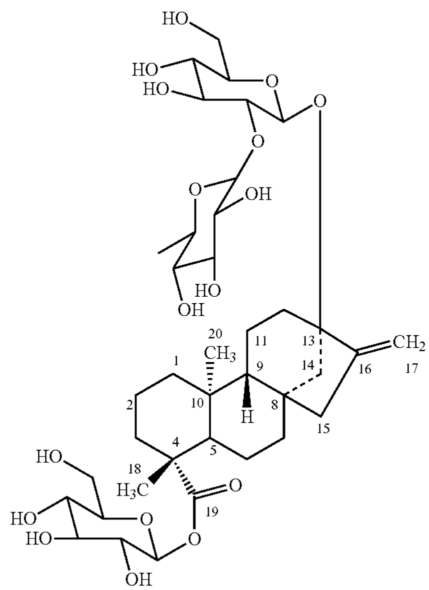 | $C_{38}H_{60}O_{17}$ | 788 |

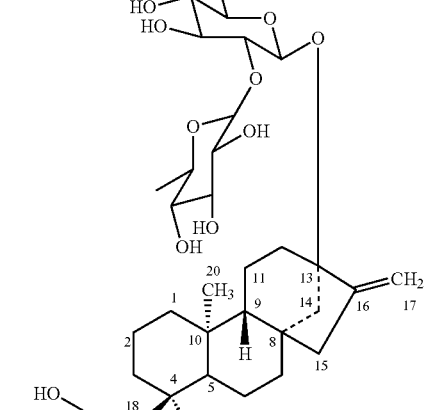

On a dry weight basis, stevioside, rebaudioside A, rebaudioside C, and dulcoside A, account for 9.1, 3.8, 0.6, and 0.3% of the total weight of the steviol glycosides in the leaves, respectively, while the other steviol glucosides are present in much lower amounts. Extracts from the *Stevia rebaudiana* plant are commercially available, which typically contain stevioside and rebaudioside A as primary compounds. The other steviol glycosides typically are present in the *stevia* extract as minor components. For example, the amount of rebaudioside A in commercial preparations can vary from about 20% to more than 90% of the total steviol glycoside content, while the amount of rebaudioside B can be about 1-2%, the amount of rebaudioside C can be about 7-15%, and the amount of rebaudioside D can be about 2% of the total steviol glycosides.

Steviol glycosides differ from each other not only by molecular structure, but also by their taste properties. For example, different steviol glycosides have different degrees of sweetness and after-taste. Stevioside, for example, is 100-150 times sweeter than sucrose, but has a bitter aftertaste. Rebaudioside A and rebaudioside E, for example, are 250-450 times sweeter than sucrose and have less of an after-taste than stevioside. Rebaudioside C is between 40-60 times sweeter than sucrose. Dulcoside A is about 30 times sweeter than sucrose.

The majority of steviol glycosides are formed by several glycosylation reactions of steviol, which are typically catalyzed by the UDP-glycosyltransferases (UGTs) using uridine 5'-diphosphoglucose (UDP-glucose) as a donor of the sugar moiety. UGTs in plants make up a very diverse group of enzymes that transfer a glucose residue from UDP-glucose to steviol. For example, glycosylation of the C-3' of the C-13-O-glucose of stevioside yields rebaudioside A; and glycosylation of the C-2' of the 19-O-glucose of the stevioside yields rebaudioside E. Further glycosylation of rebaudioside A (at C-19-O-glucose) or rebaudioside E (at C-13-O-glucose) produces rebaudioside D. (FIG. 1).

Alternative sweeteners are receiving increasing attention due to awareness of many diseases in conjunction with the consumption of high-sugar foods and beverages. Although artificial sweeteners are available, many artificial sweeteners such as dulcin, sodium cyclamate and saccharin have been banned or restricted by some countries due to concerns over their safety. Therefore, non-caloric sweeteners of natural origin are becoming increasingly popular. One of the main obstacles for the widespread use of *stevia* sweeteners are their undesirable taste attributes. Accordingly, there exists a need to develop alternative sweeteners and methods for their production to provide the best combination of sweetness potency and flavor profile.

SUMMARY OF THE DISCLOSURE

The present disclosure relates generally to natural sweeteners. More particularly, the present disclosure relates to a non-caloric sweetener and methods for synthesizing the non-caloric sweetener. The present disclosure also relates to a enzyme that can be used to prepare the non-caloric sweetener.

Steviol Glycoside—Synthetic Rebaudioside D2.

In one aspect, the present disclosure is directed to a synthetic rebaudioside (rebaudioside D2) consisting of a chemical structure:

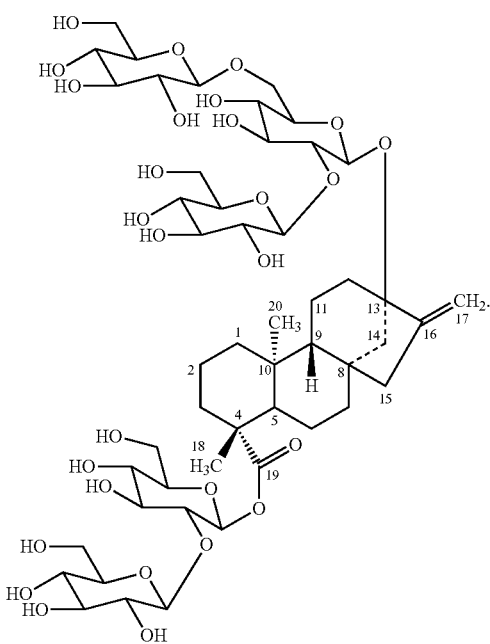

Method of Producing Rebaudioside D2 from Rebaudioside E.

In another aspect, the present disclosure is directed to a method for synthesizing rebaudioside D2 from rebaudioside E. The method comprises preparing a reaction mixture comprising rebaudioside E; a substrate selected from the group consisting of sucrose, uridine diphosphate (UDP) and uridine diphosphate-glucose (UDP-glucose); and a uridine dipospho glycosyltransferase (UDP-glycosyltransferase) selected from the group consisting of a uridine diphospho glycosyltransferase and a UDP-glycosyl transferase fusion enzyme comprising a uridine diphospho glycosyltransferase domain coupled to a sucrose synthase domain; and incubating the reaction mixture for a sufficient time to produce rebaudioside D2, wherein a glucose is covalently coupled to the rebaudioside E to produce rebaudioside D2.

Method of Producing Rebaudioside E and Rebaudioside D2 from Stevioside.

In another aspect, the present disclosure is directed to a method for synthesizing rebaudioside E and rebaudioside D2 from stevioside. The method comprises preparing a reaction mixture comprising stevioside; a substrate selected from the group consisting of sucrose, uridine diphosphate (UDP) and uridine diphosphate-glucose (UDP-glucose); and a uridine dipospho glycosyltransferase (UDP-glycosyltransferase) selected from the group consisting of a uridine diphospho glycosyltransferase and a UDP-glycosyltransferase fusion enzyme comprising a uridine diphospho glycosyltransferase domain coupled to a sucrose synthase domain; and incubating the reaction mixture for a sufficient time to produce rebaudioside E and rebaudioside D2, wherein a glucose is covalently coupled to the stevioside to produce a rebaudioside E intermediate and wherein a glucose is covalently coupled to the rebaudioside E intermediate to produce rebaudioside D2.

UDP-Glycosyltransferase Fusion Enzyme ("EUS").

In another aspect, the present disclosure is directed to a UDP-glycosyltransferase fusion enzyme (referred to herein as "EUS"). The UDP-glycosyltransferase fusion enzyme comprises a uridine diphospho glycosyltransferase domain coupled to a sucrose synthase domain. The UDP-glycosyltransferase fusion enzyme demonstrates 1,2-β glycosidic linkage and 1,6-β glycosidic linkage enzymatic activities as well as sucrose synthase activity.

Method for Producing Rebaudioside D from Rebaudioside A.

In another aspect, the present disclosure is directed to a method for synthesizing rebaudioside D from rebaudioside A. The method comprises preparing a reaction mixture comprising rebaudioside A; a substrate selected from the group consisting of sucrose, uridine diphosphate (UDP) and uridine diphosphate-glucose (UDP-glucose); and a UDP-glycosyltransferase selected from the group consisting of a uridine diphospho glycosyltransferase and a UDP-glycosyltransferase fusion enzyme (EUS) comprising a uridine diphospho glycosyltransferase domain coupled to a sucrose synthase domain; and incubating the reaction mixture for a sufficient time to produce rebaudioside D, wherein a glucose is covalently coupled to the rebaudioside A to produce rebaudioside D.

In another aspect, the present disclosure is directed to an orally consumable product comprising a sweetening amount of rebaudioside D2 selected from the group consisting of a beverage product and a consumable product.

In another aspect, the present disclosure is directed to a beverage product comprising a sweetening amount of rebaudioside D2. The rebaudioside D2 is present in the beverage product at a concentration of about 5 ppm to about 100 ppm. In some embodiments, low concentrations of rebaudioside D2, e.g., below 100 ppm, has an equivalent sweetness to sucrose solutions having concentrations between 10,000 and 30,000 ppm.

In another aspect, the present disclosure is directed to a consumable product comprising a sweetening amount of rebaudioside D2. The rebaudioside D2 is present in the consumable product at a concentration of about 5 ppm to about 100 ppm. In some embodiments, low concentrations of rebaudioside D2, e.g., below 100 ppm, has an equivalent sweetness to sucrose solutions having concentrations between 10,000 and 30,000 ppm.

In another aspect, the present disclosure is directed to a sweetener consisting of a chemical structure:

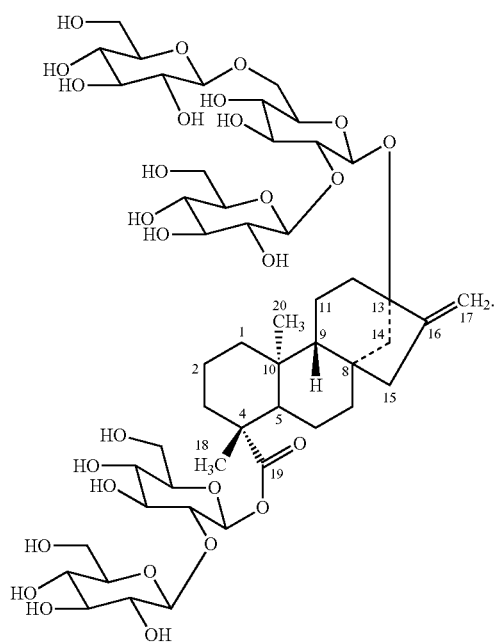

In certain embodiments that can be combined with any of the preceding embodiments, the rebaudioside D2 the only sweetener, and the product has a sweetness intensity equivalent to about 1% to about 4% (w/v-%) sucrose solution. In certain embodiments that may be combined with any of the preceding embodiments, the orally consumable product further includes an additional sweetener, where the product has a sweetness intensity equivalent to about 1% to about 10% (w/v-%) sucrose solution. In certain embodiments that may be combined with any of the preceding embodiments, every sweetening ingredient in the product is a high intensity sweetener. In certain embodiments that may be combined with any of the preceding embodiments, every sweetening ingredient in the product is a natural high intensity sweetener. In certain embodiments that may be combined with any of the preceding embodiments, the additional sweetener contains one or more sweeteners selected from a *stevia* extract, a steviol glycoside, stevioside, rebaudioside A, rebaudioside B, rebaudioside C, rebaudioside D, rebaudioside E, rebaudioside F, dulcoside A, rubusoside, steviolbioside, sucrose, high fructose corn syrup, fructose, glucose, xylose, arabinose, rhamnose, erythritol, xylitol, mannitol, sorbitol, inositol, AceK, aspartame, neotame, sucralose, saccharine, naringin dihydrochalcone (NarDHC), neohesperidin dihydrochalcone (NDHC), rubusoside, mogroside IV, siamenoside I, mogroside V, monatin, thaumatin, monellin, brazzein, L-alanine, glycine, Lo Han Guo, hernandulcin, phyllodulcin, trilobtain, and combinations thereof. In certain embodiments that may be combined with any of the preceding embodiments, the beverage product and consumable product further includes one or more additives selected from a carbohydrate, a polyol, an amino acid or salt thereof, a poly-amino acid or salt thereof, a sugar acid or salt thereof, a nucleotide, an organic acid, an inorganic acid, an organic salt, an organic acid salt, an organic base salt, an inorganic salt, a bitter compound, a flavorant, a flavoring ingredient, an astringent compound, a protein, a protein hydrolysate, a surfactant, an emulsifier, a flavonoids, an alcohol, a polymer, and combinations thereof. In certain embodiments that may be combined with any of the preceding embodiments, the rebaudioside D2 has a purity of about 50% to about 100% by weight before it is added into the product. In certain embodiments that may be combined with any of the preceding embodiments, the rebaudioside D2 in the product is a rebaudioside D2 polymorph or amorphous rebaudioside D2. In certain embodiments that may be combined with any of the preceding embodiments, the rebaudioside D2 in the product is a rebaudioside D2 stereoisomer.

Other aspects of the present disclosure relate to a method of preparing a beverage product and a consumable product by including purified rebaudioside D2 into the product or into the ingredients for making the beverage product and the consumable product, where rebaudioside D2 is present in the product at a concentration of from about 5 ppm to about 100 ppm. Other aspects of the present disclosure relate to a method for enhancing the sweetness of a beverage product and a consumable product by adding from about 5 ppm to about 100 ppm of purified rebaudioside D2 into the beverage product and the consumable product, where the added rebaudioside D2 enhances the sweetness of the beverage product and the consumable product, as compared to a corresponding a beverage product and a consumable product lacking the purified rebaudioside D2.

In certain embodiments that may be combined with any of the preceding embodiments, the rebaudioside D2 is the only sweetener, and the product has a sweetness intensity equivalent to about 1% to about 4% (w/v-%) sucrose solution. In certain embodiments that may be combined with any of the preceding embodiments, the method further includes adding an additional sweetener, where the product has a sweetness intensity equivalent to about 1% to about 10% (w/v-%) sucrose solution.

Other aspects of the present disclosure relate to a method for preparing a sweetened beverage product or a sweetened consumable product by: a) providing a beverage product or a consumable product containing one or more sweetener; and b) adding from about 5 ppm to about 100 ppm of purified rebaudioside D2 into the beverage product or the consumable product.

In certain embodiments that may be combined with any of the preceding embodiments, the method further includes adding one or more additives to the beverage product or the consumable product. In certain embodiments that may be combined with any of the preceding embodiments, the orally consumable product further contains one or more additives. In certain embodiments that may be combined with any of the preceding embodiments, the one or more additives are selected from a carbohydrate, a polyol, an amino acid or salt thereof, a poly-amino acid or salt thereof, a sugar acid or salt thereof, a nucleotide, an organic acid, an inorganic acid, an organic salt, an organic acid salt, an organic base salt, an inorganic salt, a bitter compound, a flavorant, a flavoring ingredient, an astringent compound, a protein, a protein hydrolysate, a surfactant, an emulsifier, a flavonoids, an alcohol, a polymer, and combinations thereof. In certain embodiments that may be combined with any of the preceding embodiments, every sweetening ingredient in the product is a high intensity sweetener. In certain embodiments that may be combined with any of the preceding embodiments, every sweetening ingredient in the product is a natural high intensity sweetener. In certain embodiments that may be combined with any of the preceding embodiments, the sweetener is selected from a *stevia* extract, a steviol glycoside, stevioside, rebaudioside A, rebaudioside B, rebaudioside C, rebaudioside D, rebaudioside E, rebaudioside F, dulcoside A, rubusoside, steviolbioside, sucrose, high fructose corn syrup, fructose, glucose, xylose, arabinose, rhamnose, erythritol, xylitol, mannitol, sorbitol, inositol, AceK, aspartame, neotame, sucralose, saccharine, naringin dihydrochalcone (NarDHC), neohesperidin dihydrochalcone (NDHC), rubusoside, mogroside IV, siamenoside I, mogroside V, monatin, thaumatin, monellin, brazzein, L-alanine, glycine, Lo Han Guo, hernandulcin, phyllodulcin, trilobtain, and combinations thereof. In certain embodiments that may be combined with any of the preceding embodiments, the rebaudioside D2 has a purity of about 50% to about 100% by weight before it is added into the product. In certain embodiments that may be combined with any of the preceding embodiments, the rebaudioside D2 in the product is a rebaudioside D2 polymorph or amorphous rebaudioside D2.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIGS. 3A-3G are graphs showing the HPLC retention times of stevioside ("Ste"), rebaudioside A ("Reb A") and rebaudioside D ("Reb D") standards (FIG. 3A); rebaudioside D enzymatically produced by EUS at 14 hours (FIG. 3B); rebaudioside D enzymatically produced by EUGT11 at 14 hours (FIG. 3C); rebaudioside D enzymatically produced by the UGT-SUS (EUGT11-AtSUS1) coupling system at 14 hours (FIG. 3D); rebaudioside D enzymatically produced by EUS at 24 hours (FIG. 3E); rebaudioside D enzymatically produced by EUGT11 at 24 hours (FIG. 3F); and rebaudioside D enzymatically produced by the UGT-SUS (EUGT11-AtSUS1) coupling system at 24 hours (FIG. 3G), as discussed in Example 2.

FIGS. 4A-4G are graphs showing the HPLC retention times of stevioside ("Ste"), rebaudioside A ("Reb A") and rebaudioside D ("Reb D") standards (FIG. 4A); rebaudioside D2 ("Reb D2") enzymatically produced by EUS at 14 hours (FIG. 4B); rebaudioside E ("Reb E") enzymatically produced by EUGT11 at 14 hours (FIG. 4C); rebaudioside D2 enzymatically produced by the UGT-SUS (EUGT11-AtSUS1) coupling system at 14 hours (FIG. 4D); rebaudioside D2 ("Reb D2") enzymatically produced by EUS at 24 hours (FIG. 4E); rebaudioside E ("Reb E") enzymatically produced by EUGT11 at 24 hours (FIG. 4F); and rebaudioside D2 enzymatically produced by the UGT-SUS (EUGT11-AtSUS1) coupling system at 24 hours (FIG. 4G), as discussed in Example 3.

FIGS. 6A-6B show the chemical structures of rebaudioside D2 and rebaudioside E, as discussed in Example 5.

FIGS. 8A-8C show the chemical structures of rebaudioside D2, rebaudioside E and rebaudioside D, as discussed in Example 5.

Figure 1A:
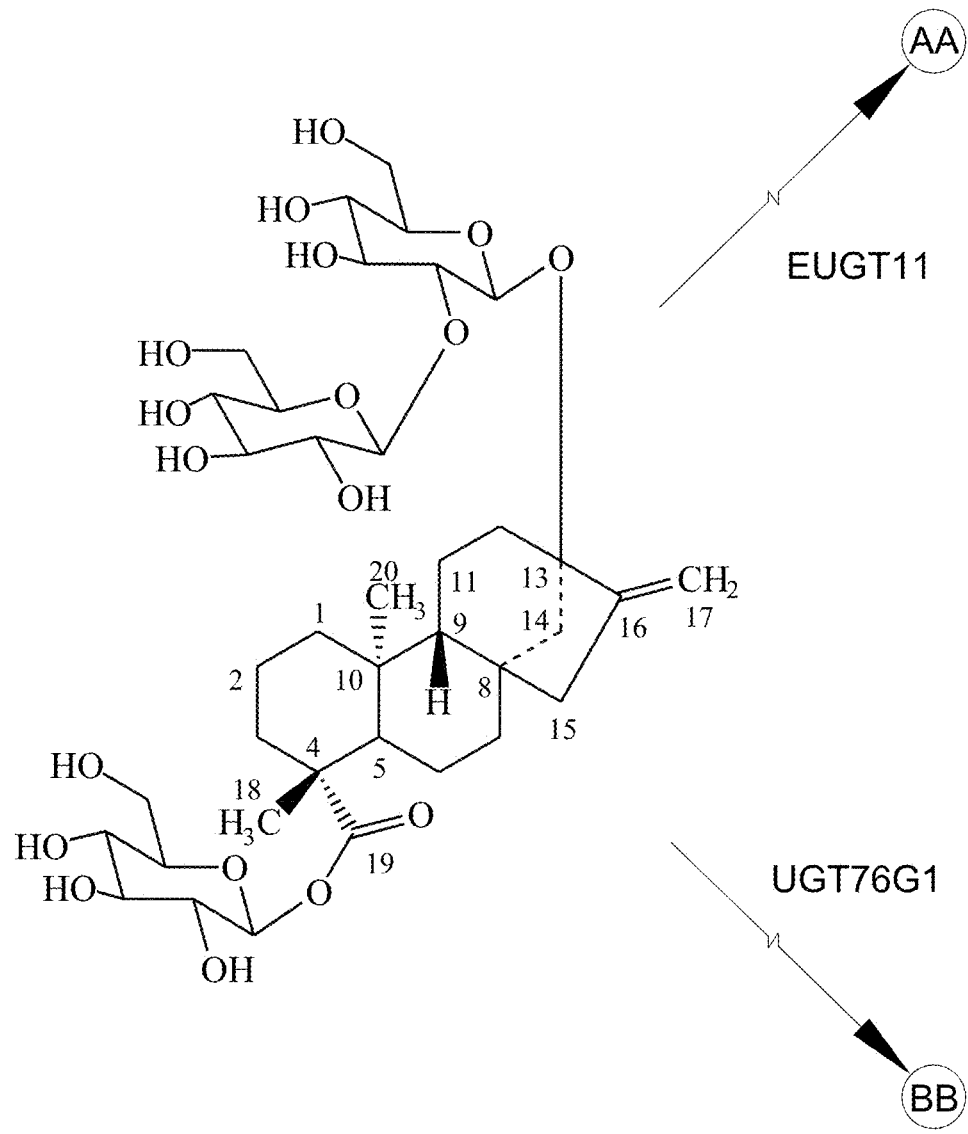
FIGS. 1A-1C are schematics illustrating the pathways of steviol glycoside biosynthesis from stevioside.
Figure 1B:
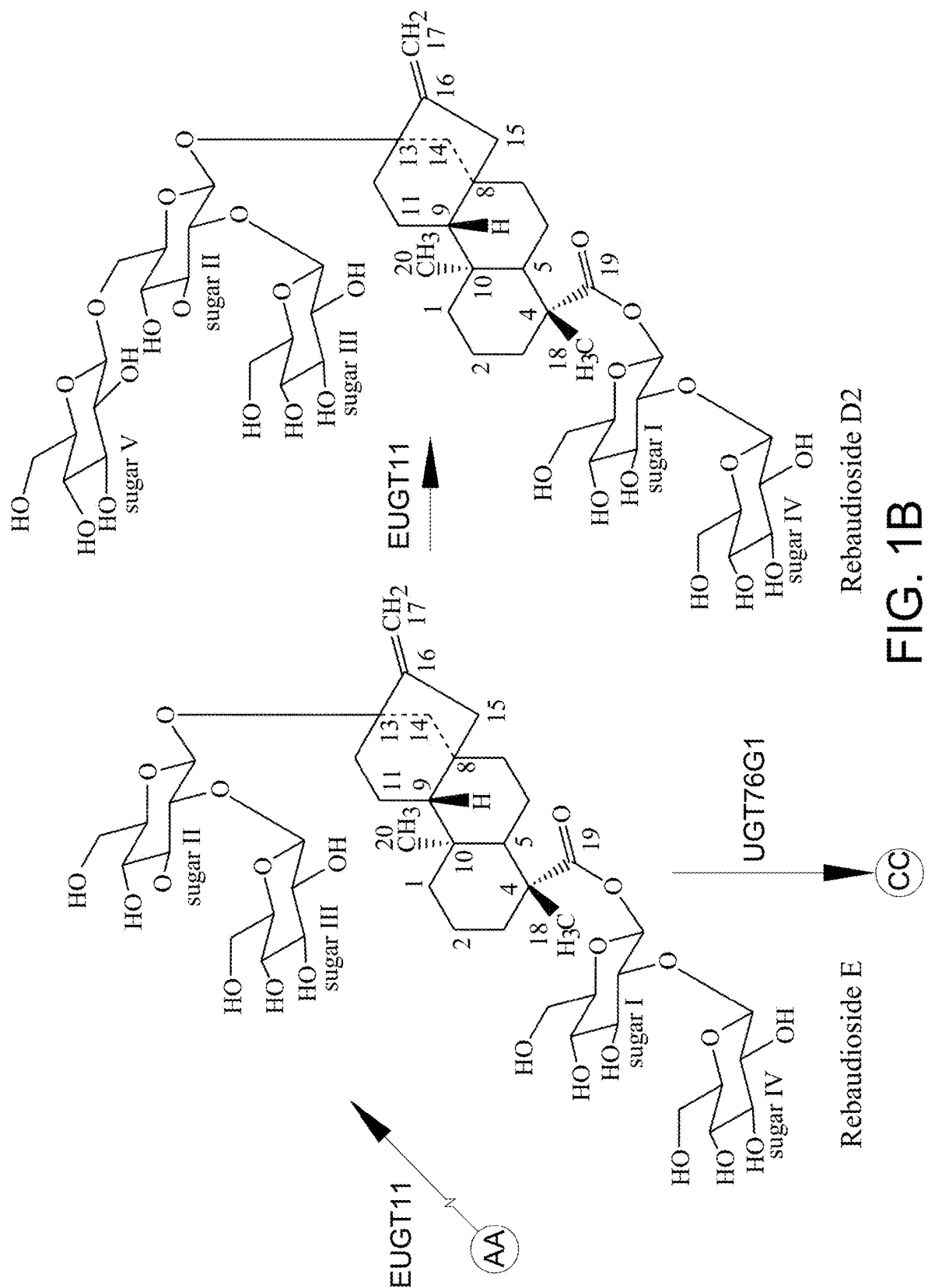
Figure 1C:
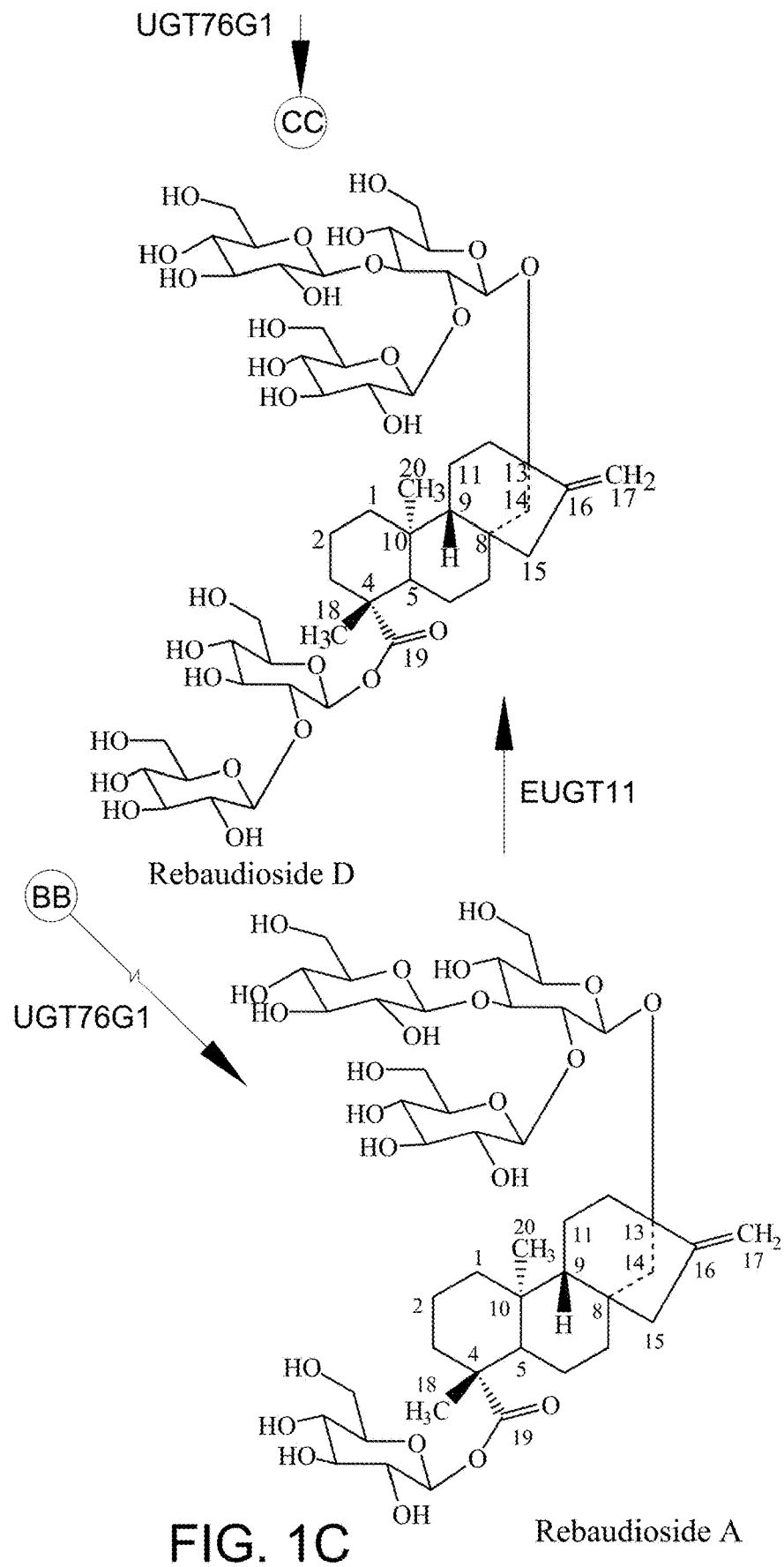

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DETAILED DESCRIPTION

Unless defined otherwise, all technical and scientific terms used herein have the same meaning as commonly understood by one of ordinary skill in the art to which the disclosure belongs. Although any methods and materials similar to or equivalent to those described herein may be used in the practice or testing of the present disclosure, the preferred materials and methods are described below.

The term "complementary" is used according to its ordinary and customary meaning as understood by a person of ordinary skill in the art, and is used without limitation to describe the relationship between nucleotide bases that are capable to hybridizing to one another. For example, with respect to DNA, adenosine is complementary to thymine and cytosine is complementary to guanine. Accordingly, the subject technology also includes isolated nucleic acid fragments that are complementary to the complete sequences as reported in the accompanying Sequence Listing as well as those substantially similar nucleic acid sequences.

The terms "nucleic acid" and "nucleotide" are used according to their respective ordinary and customary meanings as understood by a person of ordinary skill in the art, and are used without limitation to refer to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally-occurring nucleotides. Unless otherwise indicated, a particular nucleic acid sequence also implicitly encompasses conservatively modified or degenerate variants thereof (e.g., degenerate codon substitutions) and complementary sequences, as well as the sequence explicitly indicated.

The term "isolated" is used according to its ordinary and customary meaning as understood by a person of ordinary skill in the art, and when used in the context of an isolated nucleic acid or an isolated polypeptide, is used without limitation to refer to a nucleic acid or polypeptide that, by the hand of man, exists apart from its native environment and is therefore not a product of nature. An isolated nucleic acid or polypeptide can exist in a purified form or can exist in a non-native environment such as, for example, in a transgenic host cell.

The terms "incubating" and "incubation" as used herein refers to a process of mixing two or more chemical or biological entities (such as a chemical compound and an enzyme) and allowing them to interact under conditions favorable for producing a steviol glycoside composition.

The term "degenerate variant" refers to a nucleic acid sequence having a residue sequence that differs from a reference nucleic acid sequence by one or more degenerate codon substitutions. Degenerate codon substitutions can be achieved by generating sequences in which the third position of one or more selected (or all) codons is substituted with mixed base and/or deoxyinosine residues. A nucleic acid sequence and all of its degenerate variants will express the same amino acid or polypeptide.

The terms "polypeptide," "protein," and "peptide" are used according to their respective ordinary and customary meanings as understood by a person of ordinary skill in the art; the three terms are sometimes used interchangeably, and are used without limitation to refer to a polymer of amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein," "polypeptide," and "peptide" are used interchangeably herein when referring to a polynucleotide product. Thus, exemplary polypeptides include polynucleotide products, naturally occurring proteins, homologs, orthologs, paralogs, fragments and other equivalents, variants, and analogs of the foregoing.

The terms "polypeptide fragment" and "fragment," when used in reference to a reference polypeptide, are used according to their ordinary and customary meanings to a person of ordinary skill in the art, and are used without limitation to refer to a polypeptide in which amino acid residues are deleted as compared to the reference polypeptide itself, but where the remaining amino acid sequence is usually identical to the corresponding positions in the reference polypeptide. Such deletions can occur at the amino-terminus or carboxy-terminus of the reference polypeptide, or alternatively both.

The term "functional fragment" of a polypeptide or protein refers to a peptide fragment that is a portion of the full length polypeptide or protein, and has substantially the same biological activity, or carries out substantially the same function as the full length polypeptide or protein (e.g., carrying out the same enzymatic reaction).

The terms "variant polypeptide," "modified amino acid sequence" or "modified polypeptide," which are used interchangeably, refer to an amino acid sequence that is different from the reference polypeptide by one or more amino acids, e.g., by one or more amino acid substitutions, deletions, and/or additions. In an aspect, a variant is a "functional variant" which retains some or all of the ability of the reference polypeptide.

The term "functional variant" further includes conservatively substituted variants. The term "conservatively substituted variant" refers to a peptide having an amino acid sequence that differs from a reference peptide by one or more conservative amino acid substitutions, and maintains some or all of the activity of the reference peptide. A "conservative amino acid substitution" is a substitution of an amino acid residue with a functionally similar residue. Examples of conservative substitutions include the substitution of one non-polar (hydrophobic) residue such as isoleucine, valine, leucine or methionine for another; the substitution of one charged or polar (hydrophilic) residue for another such as between arginine and lysine, between glutamine and asparagine, between threonine and serine; the substitution of one basic residue such as lysine or arginine for another; or the substitution of one acidic residue, such as aspartic acid or glutamic acid for another; or the substitution of one aromatic residue, such as phenylalanine, tyrosine, or tryptophan for another. Such substitutions are expected to have little or no effect on the apparent molecular weight or isoelectric point of the protein or polypeptide. The phrase "conservatively substituted variant" also includes peptides wherein a residue is replaced with a chemically-derivatized residue, provided that the resulting peptide maintains some or all of the activity of the reference peptide as described herein.

The term "variant," in connection with the polypeptides of the subject technology, further includes a functionally active polypeptide having an amino acid sequence at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, and even 100% identical to the amino acid sequence of a reference polypeptide.

The term "homologous" in all its grammatical forms and spelling variations refers to the relationship between polynucleotides or polypeptides that possess a "common evolutionary origin," including polynucleotides or polypeptides from superfamilies and homologous polynucleotides or proteins from different species (Reeck et al., Cell 50:667, 1987). Such polynucleotides or polypeptides have sequence homology, as reflected by their sequence similarity, whether in terms of percent identity or the presence of specific amino acids or motifs at conserved positions. For example, two homologous polypeptides can have amino acid sequences that are at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, and even 100% identical.

"Percent (%) amino acid sequence identity" with respect to the variant polypeptide sequences of the subject technology refers to the percentage of amino acid residues in a candidate sequence that are identical with the amino acid residues of a reference polypeptide (such as, for example, SEQ ID NO:6), after aligning the sequences and introducing gaps, if necessary, to achieve the maximum percent sequence identity, and not considering any conservative substitutions as part of the sequence identity.

Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For example, the % amino acid sequence identity may be determined using the sequence comparison program NCBI-BLAST2. The NCBI-BLAST2 sequence comparison program may be downloaded from ncbi.nlm.nih.gov. NCBI BLAST2 uses several search parameters, wherein all of those search parameters are set to default values including, for example, unmask yes, strand=all, expected occurrences 10, minimum low complexity length=15/5, multi-pass e-value=0.01, constant for multi-pass=25, dropoff for final gapped alignment=25 and scoring matrix=BLOSUM62. In situations where NCBI-BLAST2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y where X is the number of amino acid residues scored as identical matches by the sequence alignment program NCBI-BLAST2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

In this sense, techniques for determining amino acid sequence "similarity" are well known in the art. In general, "similarity" refers to the exact amino acid to amino acid comparison of two or more polypeptides at the appropriate place, where amino acids are identical or possess similar chemical and/or physical properties such as charge or hydrophobicity. A so-termed "percent similarity" may then be determined between the compared polypeptide sequences.

Techniques for determining nucleic acid and amino acid sequence identity also are well known in the art and include determining the nucleotide sequence of the mRNA for that gene (usually via a cDNA intermediate) and determining the amino acid sequence encoded therein, and comparing this to a second amino acid sequence. In general, "identity" refers to an exact nucleotide to nucleotide or amino acid to amino acid correspondence of two polynucleotides or polypeptide sequences, respectively. Two or more polynucleotide sequences can be compared by determining their "percent identity", as can two or more amino acid sequences. The programs available in the Wisconsin Sequence Analysis Package, Version 8 (available from Genetics Computer Group, Madison, Wis.), for example, the GAP program, are capable of calculating both the identity between two polynucleotides and the identity and similarity between two polypeptide sequences, respectively. Other programs for calculating identity or similarity between sequences are known by those skilled in the art.

An amino acid position "corresponding to" a reference position refers to a position that aligns with a reference sequence, as identified by aligning the amino acid sequences. Such alignments can be done by hand or by using well-known sequence alignment programs such as ClustalW2, Blast 2, etc.

Unless specified otherwise, the percent identity of two polypeptide or polynucleotide sequences refers to the percentage of identical amino acid residues or nucleotides across the entire length of the shorter of the two sequences.

"Coding sequence" is used according to its ordinary and customary meaning as understood by a person of ordinary skill in the art, and is used without limitation to refer to a DNA sequence that encodes for a specific amino acid sequence.

"Suitable regulatory sequences" is used according to its ordinary and customary meaning as understood by a person of ordinary skill in the art, and is used without limitation to refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" is used according to its ordinary and customary meaning as understood by a person of ordinary skill in the art, and is used without limitation to refer to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different cell types, or at different stages of development, or in response to different environmental conditions. Promoters, which cause a gene to be expressed in most cell types at most times, are commonly referred to as "constitutive promoters." It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression" as used herein, is used according to its ordinary and customary meaning as understood by a person of ordinary skill in the art, and is used without limitation to refer to the transcription and stable accumulation of sense (mRNA) or antisense RNA derived from the nucleic acid fragment of the subject technology. "Overexpression" refers to the production of a gene product in transgenic or recombinant organisms that exceeds levels of production in normal or non-transformed organisms.

"Transformation" is used according to its ordinary and customary meaning as understood by a person of ordinary skill in the art, and is used without limitation to refer to the transfer of a polynucleotide into a target cell. The transferred polynucleotide can be incorporated into the genome or chromosomal DNA of a target cell, resulting in genetically stable inheritance, or it can replicate independent of the host chromosomal. Host organisms containing the transformed nucleic acid fragments are referred to as "transgenic" or "recombinant" or "transformed" organisms.

The terms "transformed," "transgenic," and "recombinant," when used herein in connection with host cells, are used according to their ordinary and customary meanings as understood by a person of ordinary skill in the art, and are used without limitation to refer to a cell of a host organism, such as a plant or microbial cell, into which a heterologous nucleic acid molecule has been introduced. The nucleic acid molecule can be stably integrated into the genome of the host cell, or the nucleic acid molecule can be present as an extrachromosomal molecule. Such an extrachromosomal molecule can be auto-replicating. Transformed cells, tissues, or subjects are understood to encompass not only the end product of a transformation process, but also transgenic progeny thereof.

The terms "recombinant," "heterologous," and "exogenous," when used herein in connection with polynucleotides, are used according to their ordinary and customary meanings as understood by a person of ordinary skill in the art, and are used without limitation to refer to a polynucleotide (e.g., a DNA sequence or a gene) that originates from a source foreign to the particular host cell or, if from the same source, is modified from its original form. Thus, a heterologous gene in a host cell includes a gene that is endogenous to the particular host cell but has been modified through, for example, the use of site-directed mutagenesis or other recombinant techniques. The terms also include non-naturally occurring multiple copies of a naturally occurring DNA sequence. Thus, the terms refer to a DNA segment that is foreign or heterologous to the cell, or homologous to the cell but in a position or form within the host cell in which the element is not ordinarily found.

Similarly, the terms "recombinant," "heterologous," and "exogenous," when used herein in connection with a polypeptide or amino acid sequence, means a polypeptide or amino acid sequence that originates from a source foreign to the particular host cell or, if from the same source, is modified from its original form. Thus, recombinant DNA segments can be expressed in a host cell to produce a recombinant polypeptide.

The terms "plasmid," "vector," and "cassette" are used according to their ordinary and customary meanings as understood by a person of ordinary skill in the art, and are used without limitation to refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

Standard recombinant DNA and molecular cloning techniques used herein are well known in the art and are described, for example, by Sambrook, J., Fritsch, E. F. and Maniatis, T. Molecular Cloning: A Laboratory Manual, $2^{nd}$ ed.; Cold Spring Harbor Laboratory: Cold Spring Harbor, N.Y., 1989 (hereinafter "Maniatis"); and by Silhavy, T. J., Bennan, M. L. and Enquist, L. W. Experiments with Gene Fusions; Cold Spring Harbor Laboratory: Cold Spring Harbor, N.Y., 1984; and by Ausubel, F. M. et al., In Current Protocols in Molecular Biology, published by Greene Publishing and Wiley-Interscience, 1987; the entireties of each of which are hereby incorporated herein by reference to the extent they are consistent herewith.

As used herein, "synthetic" or "organically synthesized" or "chemically synthesized" or "organically synthesizing" or "chemically synthesizing" or "organic synthesis" or "chemical synthesis" are used to refer to preparing the compounds through a series of chemical reactions; this does not include extracting the compound, for example, from a natural source.

The term "orally consumable product" as used herein refers to any beverage, food product, dietary supplement, nutraceutical, pharmaceutical composition, dental hygienic composition and cosmetic product which are contacted with the mouth of man or animal, including substances that are taken into and subsequently ejected from the mouth and substances which are drunk, eaten, swallowed, or otherwise ingested; and that are safe for human or animal consumption when used in a generally acceptable range of concentrations.

The term "food product" as used herein refers to fruits, vegetables, juices, meat products such as ham, bacon and sausage; egg products, fruit concentrates, gelatins and gelatin-like products such as jams, jellies, preserves, and the like; milk products such as ice cream, sour cream, yogurt, and sherbet; icings, syrups including molasses; corn, wheat, rye, soybean, oat, rice and barley products, cereal products, nut meats and nut products, cakes, cookies, confectioneries such as candies, gums, fruit flavored drops, and chocolates, chewing gum, mints, creams, icing, ice cream, pies and breads. "Food product" also refers to condiments such as herbs, spices and seasonings, flavor enhancers, such as monosodium glutamate. "Food product" further refers to also includes prepared packaged products, such as dietetic sweeteners, liquid sweeteners, tabletop flavorings, granulated flavor mixes which upon reconstitution with water provide non-carbonated drinks, instant pudding mixes, instant coffee and tea, coffee whiteners, malted milk mixes, pet foods, livestock feed, tobacco, and materials for baking applications, such as powdered baking mixes for the preparation of breads, cookies, cakes, pancakes, donuts and the like. "Food product" also refers to diet or low-calorie food and beverages containing little or no sucrose.

As used herein, the term "stereoisomer" is a general term for all isomers of individual molecules that differ only in the orientation of their atoms in space. "Stereoisomer" includes enantiomers and isomers of compounds with more than one chiral center that are not mirror images of one another (diastereomers).

As used herein, the term "amorphous rebaudioside D2" refers to a non-crystalline solid form of rebaudioside D2.

As used herein, the term "sweetness intensity" refers to the relative strength of sweet sensation as observed or experienced by an individual, e.g., a human, or a degree or amount of sweetness detected by a taster, for example on a Brix scale.

As used herein, the term "enhancing the sweetness" refers to the effect of rebaudioside D2 in increasing, augmenting, intensifying, accentuating, magnifying, and/or potentiating the sensory perception of one or more sweetness characteristics of a beverage product or a consumable product of the present disclosure without changing the nature or quality thereof, as compared to a corresponding orally consumable product that does not contain rebaudioside D2.

As used herein, the term "off-taste(s)" refers to an amount or degree of taste that is not characteristically or usually found in a beverage product or a consumable product of the present disclosure. For example, an off-taste is an undesirable taste of a sweetened consumable to consumers, such as, a bitter taste, a licorice-like taste, a metallic taste, an aversive taste, an astringent taste, a delayed sweetness onset, a lingering sweet aftertaste, and the like, etc.

As used herein, the term "w/v-%" refers to the weight of a compound, such as a sugar, (in grams) for every 100 ml of a liquid orally consumable product of the present disclosure containing such compound. As used herein, the term "w/w-%" refers to the weight of a compound, such as a sugar, (in grams) for every gram of an orally consumable product of the present disclosure containing such compound.

As used herein, the term "ppm" refers to part(s) per million by weight, for example, the weight of a compound, such as rebaudioside D2 (in milligrams) per kilogram of an orally consumable product of the present disclosure containing such compound (i.e., mg/kg) or the weight of a compound, such as rebaudioside D2 (in milligrams) per liter of an orally consumable product of the present disclosure containing such compound (i.e., mg/L); or by volume, for example the volume of a compound, such as rebaudioside D2 (in milliliters) per liter of an orally consumable product of the present disclosure containing such compound (i.e., ml/L).

In accordance with the present disclosure, a non-caloric sweetener and methods for synthesizing the non-caloric sweetener are disclosed. Also in accordance with the present disclosure an enzyme and methods of using the enzyme to prepare the non-caloric sweetener are disclosed.

Synthetic Non-Caloric Sweetener: Synthetic Rebaudioside D2

In one aspect, the present disclosure is directed to a synthetic non-caloric sweetener. The synthetic non-caloric sweetener is a synthetic rebaudioside-type steviol glycoside and has been given the name, "Rebaudioside D2". As illustrated in the chemical structure (I) below, rebaudioside D2 ("Reb D2") is a steviol glycoside having five glycosidic residues similar to the five glycosidic residues of the steviol glycoside, rebaudioside D.

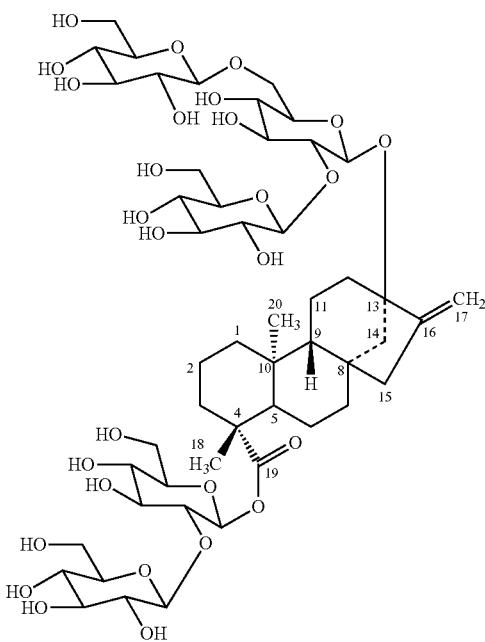

(I)

Rebaudioside D2 has the molecular formula $C_{50}H_{80}O_{28}$ and the IUPAC name, 13-[(2-O-β-D-glucopyranosyl-6-O-β-D-glucopyranosyl-6-D-glucopyranosyl)oxy] ent-kaur-16-en-19-oic acid-(2-O-β-D-glucopyranosyl-β-D-glucopyranosyl) ester.

As illustrated in the chemical structures for rebaudioside D2, rebaudioside E and rebaudioside D, rebaudioside D2 and rebaudioside D have five (3-D-glucosyl units connected to the aglycone steviol in the structure, whereas rebaudioside E contains four D-glycosidic residues (see e.g., Table 1 and FIG. 8). The synthesized rebaudioside D2 includes two glycosidic residues at the C19 position and three glycosidic residues at the C13 position of steviol. In comparison, rebaudioside D also includes five glycosidic residues; two glycosidic residues at the C19 position and three glycosidic residues at the C13 position of the aglycone steviol. The fifth glycosidic residue ("sugar V") of rebaudioside D2 is positioned at the C-6' of the C13 O-glucose of Reb E by a 1,6 β glycosidic linkage, whereas the fifth glycosidic residue ("sugar V") of rebaudioside D is positioned at the C-3' of the C13 O-glucose of Reb E by a 1,3 β glycosidic linkage (see, FIG. 8). Rebaudioside E, however, includes two glycosidic residues at the C19 position and two glycosidic residues at the C13 position. Without being bound by theory, it is believed that steviol glycosides having 5 glycosidic residues (rebaudioside D) and 4 glycosidic residues (rebaudioside A and rebaudioside E) have significantly better taste quality than steviol glycosides having less glycosidic residues (stevioside and rubusoside).

Methods of Producing Rebaudioside D2

In another aspect, the present disclosure is directed to a method for synthesizing rebaudioside D2 from rebaudioside E. In one embodiment, the method includes preparing a reaction mixture including rebaudioside E; a substrate selected from the group consisting of sucrose, uridine diphosphate (UDP) and uridine diphosphate-glucose (UDP-glucose); and a UDP-glycosyltransferase selected from a uridine diphospho glycosyltransferase and a UDP-glycosyltransferase fusion enzyme (EUS) comprising a uridine-diphospho (UDP) glycosyltransferase domain coupled to a sucrose synthase domain; and incubating the reaction mixture for a sufficient time to produce rebaudioside D2, wherein a glucose is covalently coupled to the rebaudioside E to produce rebaudioside D2.

A particularly suitable a uridine diphospho (UDP) glycosyltransferase can be, for example, EUGT11 (as described in WO 2013022989). EUGT11 is a uridine 5'-diphosphate-dependent glycosyl transferase ("UGT") having 1,2-19-O-glucose and 1,2-13-O-glucose glycosylation activity. EUGT11 is known to catalyze the production of stevioside to rebaudioside E and rebaudioside A to rebaudioside D. Surprisingly and unexpectedly, however, it has been discovered that uridine diphospho (UDP) glycosyltransferase can be used in vitro to convert rebaudioside E into rebaudioside D2.

A suitable uridine diphospho glycosyltransferase can be, for example, an *Oryza sativa* uridine diphospho glycosyltransferase EUGT11. A particularly suitable uridine diphospho glycosyltransferase has the amino acid sequence of SEQ ID NO:1.

The method can further include adding a sucrose synthase to the reaction mixture that contains the uridine diphospho (UDP) glycosyltransferase. Addition of the sucrose synthase to the reaction mixture that includes a uridine diphospho glycosyltransferase creates a "UGT-SUS coupling system". In the UGT-SUS coupling system, UDP-glucose can be regenerated from UDP and sucrose, which allows for omitting the addition of extra UDP-glucose to the reaction mixture or using UDP in the reaction mixture.

Suitable sucrose synthase domains can be for example, an *Arabidopsis* sucrose synthase 1; a *Coffea* sucrose synthase 1 and a *Stevia* sucrose synthase 1. A particularly suitable sucrose synthase domain can be, for example, *Arabidopsis* sucrose synthase 1. A particularly suitable *Arabidopsis* sucrose synthase 1 is *Arabidopsis thaliana* sucrose synthase 1 (AtSUS1). A particularly suitable sucrose synthase 1 can be, for example, a sucrose synthase 1 having the amino acid sequence of SEQ ID NO:3.

In another embodiment, the UDP-glycosyltransferase can be a UDP-glycosyltransferase fusion enzyme (also referred to herein as "EUS") that includes a uridine diphospho glycosyltransferase domain coupled to a sucrose synthase domain. The UDP-glycosyltransferase fusion enzyme is described in more detail below.

In the reaction, the UDP-glycosyltransferase (for example, EUGT11 and EUS) has a 1,6-13 O glucose glycosylation activity and, in one embodiment, can transfer a glucose molecule to rebaudioside E to form rebaudioside D2. The UDP-glycosyltransferase (for example, EUGT11 and EUS) also has 1,2-19 O-glucose and 1,2-13-O-glucose glycosylation activity. In another embodiment, the UDP-glycosyltransferase can transfer a glucose molecule to stevioside to form rebaudioside E and can also transfer a glucose molecule to rebaudioside A to form rebaudioside D. Additionally, the EUS fusion enzyme has sucrose synthase activity, and thus, can regenerate UDP-glucose from UDP and sucrose.

A particularly suitable embodiment is directed to a method of producing rebaudioside D2 from rebaudioside E using a UGT-SUS coupling system. The method includes preparing a reaction mixture including rebaudioside E; sucrose; uridine diphosphate (UDP); a uridine diphospho glycosyltransferase; and a sucrose synthase; and incubating the reaction mixture for a sufficient time to produce rebaudioside D2, wherein a glucose is covalently coupled to the rebaudioside E to produce rebaudioside D2.

Suitable UDP glycosyltransferases for use in the method of this embodiment is the same as described above. Suitable sucrose synthases for use in the method of this embodiment is the same as described above.

Another particularly suitable embodiment is directed to a method of producing rebaudioside D2 from rebaudioside E using a UDP-glycosyltransferase fusion enzyme that includes a uridine diphospho glycosyltransferase domain coupled to a sucrose synthase domain. The method includes preparing a reaction mixture including rebaudioside E; sucrose; uridine diphosphate (UDP); and a UDP-glycosyltransferase fusion enzyme that includes a uridine diphospho glycosyltransferase domain coupled to a sucrose synthase domain; and incubating the reaction mixture for a sufficient time to produce rebaudioside D2, wherein a glucose is covalently coupled to the rebaudioside E to produce rebaudioside D2.

A particularly suitable UDP-glycosyltransferase fusion enzyme is described in more detail below.

In another aspect, the present disclosure is directed to a method for synthesizing rebaudioside D2 from stevioside. The method for synthesizing rebaudioside D2 from stevioside includes preparing a reaction mixture including stevioside; a substrate selected from the group consisting of sucrose, uridine diphosphate (UDP) and uridine diphosphate-glucose (UDP-glucose); and a UDP-glycosyltransferase selected from the group consisting of a uridine diphospho glycosyltransferase and a UDP-glycosyltransferase fusion enzyme that includes a uridine diphospho glycosyltransferase domain coupled to a sucrose synthase domain; and incubating the reaction mixture for a sufficient time to produce rebaudioside D2, wherein a glucose is covalently coupled to the stevioside to produce a rebaudioside E intermediate, and wherein a glucose is covalently coupled to the rebaudioside E intermediate to produce rebaudioside D2.

Initially, the UDP glycosyltransferase for use in the method of this embodiment is the same as described above. As described above, the method may further include adding a sucrose synthase to the reaction mixture that contains the uridine diphospho glycosyltransferase to create a UGT-SUS coupling system.

A particularly suitable embodiment is directed to a method of producing rebaudioside D2 from stevioside using a UGT-SUS coupling system. The method includes preparing a reaction mixture including stevioside; sucrose; uridine diphosphate (UDP); a uridine diphospho glycosyltransferase; and a sucrose synthase; and incubating the reaction mixture for a sufficient time to produce rebaudioside D2, wherein a glucose is covalently coupled to the stevioside to produce a rebaudioside E intermediate, and wherein a glucose is covalently coupled to the rebaudioside E intermediate to produce rebaudioside D2.

Suitable UDP glycosyltransferases for use in the method of this embodiment is the same as described above. Suitable sucrose synthases for use in the method of this embodiment is the same as described above.

Another particularly suitable embodiment is directed to a method of producing rebaudioside D2 from stevioside using a UDP-glycosyltransferase fusion enzyme that includes a uridine diphospho glycosyltransferase domain coupled to a sucrose synthase domain. The method includes preparing a reaction mixture including stevioside; a substrate selected from the group consisting of sucrose; uridine diphosphate (UDP); and a UDP-glycosyltransferase fusion enzyme that includes a uridine diphospho glycosyltransferase domain coupled to a sucrose synthase domain; and incubating the reaction mixture for a sufficient time to produce rebaudioside D2, wherein a glucose is covalently coupled to the stevioside to produce a rebaudioside E intermediate, and wherein a glucose is covalently coupled to the rebaudioside E intermediate to produce rebaudioside D2.

A particularly suitable UDP-glycosyltransferase fusion enzyme is described in more detail below.

UDP-Glycosyltransferase Fusion Enzyme

In another aspect, the present disclosure is directed to a UDP-glycosyltransferase fusion enzyme (also referred to herein as "EUS"). In particular, the UDP-glycosyltransferase fusion enzyme includes a uridine diphospho glycosyltransferase domain coupled to a sucrose synthase domain. The EUS fusion enzyme has a 1,2-19 O-glucose glycosylation activity. Surprisingly and unexpectedly, the EUS fusion enzyme also has a 1,6-13 O-glucose glycosylation activity that can transfer a glucose molecule to rebaudioside E to form rebaudioside D2. Additionally, the EUS fusion enzyme has sucrose synthase activity, and thus, can regenerate UDP-glucose from UDP and sucrose.

The UDP-glycosyltransferase fusion enzyme can have a polypeptide sequence with at least 70%, at least 80%, at least 85%, at least 90%, at least 91%, at least 92%, at least 93%, at least 94%, at least 95%, at least 96%, at least 97%, at least 98%, at least 99% and even 100% identical to the amino acid sequence set forth in SEQ ID NO:5. Suitably, the amino acid sequence of the UDP-glycosyltransferase fusion enzyme has at least 80% identity to SEQ ID No:5. More suitably, the amino acid sequence of the UDP-glycosyltransferase fusion enzyme has at least 85%, at least 90%, at least 91%, at least 92%, at least 93%, at least 94%, at least 95%, at least 96%, at least 97%, at least 98%, at least 99%, and even 100% amino acid sequence identity to the amino acid sequence set forth in SEQ ID NO:5.

In another aspect, the present disclosure relates to an isolated nucleic acid having a nucleotide sequence encoding the UDP-glycosyltransferase fusion enzyme described herein. For example, the isolated nucleic acid can include a nucleotide sequence encoding a polypeptide of the UDP-glycosyltransferase fusion enzyme having a nucleic acid sequence that has at least 70%, at least 75%, at least 80%, at least 85%, at least 90%, at least 91%, at least 92%, at least 93%, at least 94%, at least 95%, at least 96%, at least 97%, at least 98%, at least 99%, and even 100% sequence homology to the nucleic acid sequence set forth in SEQ ID NO:6. Suitably, the isolated nucleic acid includes a nucleotide sequence encoding a polypeptide of the UDP-glycosyltransferase fusion enzyme having an amino acid sequence that is at least 80% sequence identity to the amino acid sequence set forth in SEQ ID NO:5. More suitably, the isolated nucleic acid includes a nucleotide sequence encoding a polypeptide of the UDP-glycosyltransferase fusion enzyme having an amino acid sequence that has at least 85%, at least 90%, at least 91%, at least 92%, at least 93%, at least 94%, at least 95%, at least 96%, at least 97%, at least 98%, at least 99%, and even 100% sequence identity to the amino acid sequence set forth in SEQ ID NO:5. The isolated nucleic acid thus includes those nucleotide sequences encoding functional fragments of SEQ ID NO:5, functional variants of SEQ ID NO:5, or other homologous polypeptides that have, for example, at least 80%, at least 85%, at least 90%, at least 91%, at least 92%, at least 93%, at least 94%, at least 95%, at least 96%, at least 97%, at least 98%, at least 99%, and even 100% sequence identity to SEQ ID NO:5. As known by those skilled in the art, the nucleic acid sequence encoding the UDP-glycosyltransferase can be codon optimized for expression in a suitable host organism such as, for example, bacteria and yeast.

A suitable uridine diphospho glycosyltransferase domain can be an *Oryza sativa* uridine diphospho glycosyltransferase EUGT11 (GenBank Accession No. AC133334). A particularly suitable uridine diphospho glycosyltransferase EUGT11 can be, for example, the uridine diphospho glycosyltransferase EUGT11 domain having an amino acid sequence of SEQ ID NO:1.

Suitable sucrose synthase domains can be for example, an *Arabidopsis* sucrose synthase 1; a *Coffea* sucrose synthase 1 and a *Stevia* sucrose synthase 1. A particularly suitable sucrose synthase domain can be, for example, *Arabidopsis* sucrose synthase 1. A particularly suitable *Arabidopsis* sucrose synthase 1 is *Arabidopsis thaliana* sucrose synthase 1 (AtSUS1). A particularly suitable sucrose synthase 1 domain can be, for example, a sucrose synthase 1 having the amino acid sequence of SEQ ID NO:3.

Sucrose synthase catalyzes the chemical reaction between NDP-glucose and D-fructose to produce NDP and sucrose. Sucrose synthase is a glycosyltransferase. The systematic name of this enzyme class is NDP-glucose:D-fructose 2-alpha-D-glucosyltransferase. Other names in common use include UDP glucose-fructose glucosyltransferase, sucrose synthetase, sucrose-UDP glucosyltransferase, sucrose-uridine diphosphate glucosyltransferase, and uridine diphosphoglucose-fructose glucosyltransferase.

Methods of Producing Rebaudioside D

In another aspect, the present disclosure is directed to a method for synthesizing rebaudioside D. The method includes preparing a reaction mixture including rebaudioside A; a substrate selected from the group consisting of sucrose, uridine diphosphate (UDP) and uridine diphosphate-glucose (UDP-glucose); and a UDP-glycosyltransferase selected from the group consisting of uridine diphospho glycosyltransferase and a UDP-glycosyltransferase fusion enzyme (EUS) that includes a uridine diphospho glycosyltransferase domain coupled to a sucrose synthase domain; and incubating the reaction mixture for a sufficient time to produce rebaudioside D, wherein a glucose is covalently coupled to the rebaudioside A to produce rebaudioside D.

In the embodiment wherein the UDP-glycosyltransferase is uridine diphospho glycosyltransferase, a suitable uridine diphospho glycosyltransferase can be an *Oryza sativa* uridine diphospho glycosyltransferase EUGT11 (GenBank Accession No. AC133334). A particularly suitable uridine diphospho glycosyltransferase can be, for example, the uridine diphospho glycosyltransferase having an amino acid sequence of SEQ ID NO:1.

In the embodiment wherein the UDP-glycosyltransferase is a uridine diphospho glycosyltransferase, the method can further include adding a sucrose synthase to the reaction mixture. Suitable sucrose synthases can be for example, an *Arabidopsis* sucrose synthase 1; a *Coffea* sucrose synthase 1 and a *Stevia* sucrose synthase 1. A particularly suitable sucrose synthase can be, for example, *Arabidopsis* sucrose synthase 1. A particularly suitable *Arabidopsis* sucrose synthase 1 is *Arabidopsis thaliana* sucrose synthase 1 (AtSUS1). A particularly suitable sucrose synthase 1 can be, for example, a sucrose synthase 1 having the amino acid sequence of SEQ ID NO:3.

In the embodiment wherein the UDP-glycosyltransferase is a UDP-glycosyltransferase fusion enzyme (EUS) that includes a uridine diphospho glycosyltransferase domain coupled to a sucrose synthase domain as described above, a suitable uridine diphospho glycosyltransferase domain can be an *Oryza sativa* uridine diphospho glycosyltransferase EUGT11 (GenBank Accession No. AC133334). A particularly suitable uridine diphospho glycosyltransferase domain can be, for example, a uridine diphospho glycosyltransferase domain having an amino acid sequence of SEQ ID NO:1. A particularly suitable sucrose synthase 1 domain can have, for example, an amino acid sequence of SEQ ID NO:3. A particularly suitable UDP-glycosyltransferase fusion enzyme (EUS) can have, for example, an amino acid sequence of SEQ ID NO:5.

A particularly suitable embodiment is directed to a method for synthesizing rebaudioside D using a UGT-SUS coupling system. The method includes preparing a reaction mixture including rebaudioside A; sucrose; uridine diphosphate (UDP); a UDP-glycosyltransferase; and a sucrose synthase; and incubating the reaction mixture for a sufficient time to produce rebaudioside D, wherein a glucose is covalently coupled to the rebaudioside A to produce rebaudioside D.

Suitable UDP glycosyltransferases for use in the method of this embodiment is the same as described above. Suitable sucrose synthases for use in the method of this embodiment is the same as described above.

A particularly suitable embodiment is directed to a method for synthesizing rebaudioside D using a UDP-glycosyltransferase fusion enzyme. The method includes preparing a reaction mixture including rebaudioside A; sucrose; uridine diphosphate (UDP); and a UDP-glycosyltransferase fusion enzyme (EUS) that includes a uridine diphospho glycosyltransferase domain coupled to a sucrose synthase domain; and incubating the reaction mixture for a sufficient time to produce rebaudioside D, wherein a glucose is covalently coupled to the rebaudioside A to produce rebaudioside D.

A particularly suitable UDP-glycosyltransferase fusion enzyme is described in more detail above.

Orally Consumable Products

In another aspect, the present disclosure is directed to an orally consumable product having a sweetening amount of rebaudioside D2, selected from the group consisting of a beverage product and a consumable product.

The orally consumable product can have a sweetness intensity equivalent to about 1% (w/v-%) to about 4% (w/v-%) sucrose solution.

The orally consumable product can have from about 5 ppm to about 100 ppm rebaudioside D2.

The rebaudioside D2 can be the only sweetener in the orally consumable product.

The orally consumable product can also have at least one additional sweetener. The at least one additional sweetener can be a natural high intensity sweetener, for example. The additional sweetener can be selected from a *stevia* extract, a steviol glycoside, stevioside, rebaudioside A, rebaudioside B, rebaudioside C, rebaudioside D, rebaudioside E, rebaudioside F, dulcoside A, rubusoside, steviolbioside, sucrose, high fructose corn syrup, fructose, glucose, xylose, arabinose, rhamnose, erythritol, xylitol, mannitol, sorbitol, inositol, AceK, aspartame, neotame, sucralose, saccharine, naringin dihydrochalcone (NarDHC), neohesperidin dihydrochalcone (NDHC), rubusoside, mogroside IV, siamenoside I, mogroside V, monatin, thaumatin, monellin, brazzein, L-alanine, glycine, Lo Han Guo, hernandulcin, phyllodulcin, trilobtain, and combinations thereof.

The orally consumable product can also have at least one additive. The additive can be, for example, a carbohydrate, a polyol, an amino acid or salt thereof, a polyamino acid or salt thereof, a sugar acid or salt thereof, a nucleotide, an organic acid, an inorganic acid, an organic salt, an organic acid salt, an organic base salt, an inorganic salt, a bitter compound, a flavorant, a flavoring ingredient, an astringent compound, a protein, a protein hydrolysate, a surfactant, an emulsifier, a flavonoids, an alcohol, a polymer, and combinations thereof.

In one aspect, the present disclosure is directed to a beverage product comprising a sweetening amount of rebaudioside D2.

The beverage product can be, for example, a carbonated beverage product and a non-carbonated beverage product. The beverage product can also be, for example, a soft drink, a fountain beverage, a frozen beverage; a ready-to-drink beverage; a frozen and ready-to-drink beverage, coffee, tea, a dairy beverage, a powdered soft drink, a liquid concentrate, flavored water, enhanced water, fruit juice, a fruit juice flavored drink, a sport drink, and an energy drink.

In some embodiments, a beverage product of the present disclosure can include one or more beverage ingredients such as, for example, acidulants, fruit juices and/or vegetable juices, pulp, etc., flavorings, coloring, preservatives, vitamins, minerals, electrolytes, erythritol, tagatose, glycerine, and carbon dioxide. Such beverage products may be provided in any suitable form, such as a beverage concentrate and a carbonated, ready-to-drink beverage.

In certain embodiments, beverage products of the present disclosure can have any of numerous different specific formulations or constitutions. The formulation of a beverage product of the present disclosure can vary to a certain extent, depending upon such factors as the product's intended market segment, its desired nutritional characteristics, flavor profile, and the like. For example, in certain embodiments, it can generally be an option to add further ingredients to the formulation of a particular beverage product. For example, additional (i.e., more and/or other) sweeteners can be added, flavorings, electrolytes, vitamins, fruit juices or other fruit products, tastents, masking agents and the like, flavor enhancers, and/or carbonation typically may be added to any such formulations to vary the taste, mouthfeel, nutritional characteristics, etc. In embodiments, the beverage product can be a cola beverage that contains water, about 5 ppm to about 100 ppm rebaudioside D2, an acidulant, and flavoring. Exemplary flavorings can be, for example, cola flavoring, citrus flavoring, and spice flavorings. In some embodiments, carbonation in the form of carbon dioxide can be added for effervescence. In other embodiments, preservatives can be added, depending upon the other ingredients, production technique, desired shelf life, etc. In certain embodiments, caffeine can be added. In some embodiments, the beverage product can be a cola-flavored carbonated beverage, characteristically containing carbonated water, sweetener, kola nut extract and/or other flavoring, caramel coloring, one or more acids, and optionally other ingredients.

Suitable amounts of rebaudioside D2 present in the beverage product can be, for example, from about 5 ppm to about 100 ppm. In some embodiments, low concentrations of rebaudioside D2, for example, less than 100 ppm, and has an equivalent sweetness to sucrose solutions having concentrations between 10,000 ppm to 30,000 ppm. The final concentration that ranges from about 5 ppm to about 100 ppm, from about 5 ppm to about 95 ppm, from about 5 ppm to about 90 ppm, from about 5 ppm to about 85 ppm, from about 5 ppm to about 80 ppm, from about 5 ppm to about 75 ppm, from about 5 ppm to about 70 ppm, from about 5 ppm to about 65 ppm, from about 5 ppm to about 60 ppm, from about 5 ppm to about 55 ppm, from about 5 ppm to about 50 ppm, from about 5 ppm to about 45 ppm, from about 5 ppm to about 40 ppm, from about 5 ppm to about 35 ppm, from about 5 ppm to about 30 ppm, from about 5 ppm to about 25 ppm, from about 5 ppm to about 20 ppm, from about 5 ppm to about 15 ppm, or from about 5 ppm to about 10 ppm. Alternatively, rebaudioside D2 can be present in beverage products of the present disclosure at a final concentration that ranges from about 5 ppm to about 100 ppm, from about 10 ppm to about 100 ppm, from about 15 ppm to about 100 ppm, from about 20 ppm to about 100 ppm, from about 25 ppm to about 100 ppm, from about 30 ppm to about 100 ppm, from about 35 ppm to about 100 ppm, from about 40 ppm to about 100 ppm, from about 45 ppm to about 100 ppm, from about 50 ppm to about 100 ppm, from about 55 ppm to about 100 ppm, from about 60 ppm to about 100 ppm, from about 65 ppm to about 100 ppm, from about 70 ppm to about 100 ppm, from about 75 ppm to about 100 ppm, from about 80 ppm to about 100 ppm, from about 85 ppm to about 100 ppm, from about 90 ppm to about 100 ppm, or from about 95 ppm to about 100 ppm.

In another aspect, the present disclosure is directed to a consumable comprising a sweetening amount of rebaudioside D2. The consumable can be, for example, a food product, a nutraceutical, a pharmaceutical, a dietary supplement, a dental hygienic composition, an edible gel composition, a cosmetic product and a tabletop flavoring.

As used herein, "dietary supplement(s)" refers to compounds intended to supplement the diet and provide nutrients, such as vitamins, minerals, fiber, fatty acids, amino acids, etc. that may be missing or may not be consumed in sufficient quantities in a diet. Any suitable dietary supplement known in the art may be used. Examples of suitable dietary supplements can be, for example, nutrients, vitamins, minerals, fiber, fatty acids, herbs, botanicals, amino acids, and metabolites.

As used herein, "nutraceutical(s)" refers to compounds, which includes any food or part of a food that may provide medicinal or health benefits, including the prevention and/or treatment of disease or disorder (e.g., fatigue, insomnia, effects of aging, memory loss, mood disorders, cardiovascular disease and high levels of cholesterol in the blood, diabetes, osteoporosis, inflammation, autoimmune disorders, etc.). Any suitable nutraceutical known in the art may be used. In some embodiments, nutraceuticals can be used as supplements to food and beverages and as pharmaceutical formulations for enteral or parenteral applications which may be solid formulations, such as capsules or tablets, or liquid formulations, such as solutions or suspensions.

In some embodiments, dietary supplements and nutraceuticals can further contain protective hydrocolloids (such as gums, proteins, modified starches), binders, film-forming agents, encapsulating agents/materials, wall/shell materials, matrix compounds, coatings, emulsifiers, surface active agents, solubilizing agents (oils, fats, waxes, lecithins, etc.), adsorbents, carriers, fillers, co-compounds, dispersing agents, wetting agents, processing aids (solvents), flowing agents, taste-masking agents, weighting agents, jellyfying agents, gel-forming agents, antioxidants and antimicrobials.

As used herein, a "gel" refers to a colloidal system in which a network of particles spans the volume of a liquid medium. Although gels mainly are composed of liquids, and thus exhibit densities similar to liquids, gels have the structural coherence of solids due to the network of particles that spans the liquid medium. For this reason, gels generally appear to be solid, jelly-like materials. Gels can be used in a number of applications. For example, gels can be used in foods, paints, and adhesives. Gels that can be eaten are referred to as "edible gel compositions." Edible gel compositions typically are eaten as snacks, as desserts, as a part of staple foods, or along with staple foods. Examples of suitable edible gel compositions can be, for example, gel desserts, puddings, jams, jellies, pastes, trifles, aspics, marshmallows, gummy candies, and the like. In some embodiments, edible gel mixes generally are powdered or granular solids to which a fluid may be added to form an edible gel composition. Examples of suitable fluids can be, for example, water, dairy fluids, dairy analogue fluids, juices, alcohol, alcoholic beverages, and combinations thereof. Examples of suitable dairy fluids can be, for example, milk, cultured milk, cream, fluid whey, and mixtures thereof. Examples of suitable dairy analogue fluids can be, for example, soy milk and non-dairy coffee whitener.

As used herein, the term "gelling ingredient" refers to any material that can form a colloidal system within a liquid medium. Examples of suitable gelling ingredients can be, for example, gelatin, alginate, carageenan, gum, pectin, konjac, agar, food acid, rennet, starch, starch derivatives, and combinations thereof. It is well known to those in the art that the amount of gelling ingredient used in an edible gel mix or an edible gel composition can vary considerably depending on a number of factors such as, for example, the particular gelling ingredient used, the particular fluid base used, and the desired properties of the gel.

Gel mixes and gel compositions of the present disclosure can be prepared by any suitable method known in the art. In some embodiments, edible gel mixes and edible gel compositions of the present disclosure can be prepared using other ingredients in addition to rebaudioside D2 and the gelling agent. Examples of other suitable ingredients can be, for example, a food acid, a salt of a food acid, a buffering system, a bulking agent, a sequestrant, a cross-linking agent, one or more flavors, one or more colors, and combinations thereof.

Any suitable pharmaceutical composition known in the art may be used. In certain embodiments, a pharmaceutical composition of the present disclosure can contain from about 5 ppm to about 100 ppm of rebaudioside D2, and one or more pharmaceutically acceptable excipients. In some embodiments, pharmaceutical compositions of the present disclosure can be used to formulate pharmaceutical drugs containing one or more active agents that exert a biological effect. Accordingly, in some embodiments, pharmaceutical compositions of the present disclosure can contain one or more active agents that exert a biological effect. Suitable active agents are well known in the art (e.g., The Physician's Desk Reference). Such compositions can be prepared according to procedures well known in the art, for example, as described in Remington's Pharmaceutical Sciences, Mack Publishing Co., Easton, Pa., USA.

Rebaudioside D2 can be used with any suitable dental and oral hygiene compositions known in the art. Examples of suitable dental and oral hygiene compositions can be, for example, toothpastes, tooth polishes, dental floss, mouthwashes, mouthrinses, dentrifices, mouth sprays, mouth refreshers, plaque rinses, dental pain relievers, and the like.

Suitable amounts of rebaudioside D2 present in the consumable can be, for example, from about 5 parts per million (ppm) to about 100 parts per million (ppm). In some embodiments, low concentrations of rebaudioside D2, for example, less than 100 ppm, has an equivalent sweetness to sucrose solutions having concentrations between 10,000 ppm to 30,000 ppm. The final concentration that ranges from about 5 ppm to about 100 ppm, from about 5 ppm to about 95 ppm, from about 5 ppm to about 90 ppm, from about 5 ppm to about 85 ppm, from about 5 ppm to about 80 ppm, from about 5 ppm to about 75 ppm, from about 5 ppm to about 70 ppm, from about 5 ppm to about 65 ppm, from about 5 ppm to about 60 ppm, from about 5 ppm to about 55 ppm, from about 5 ppm to about 50 ppm, from about 5 ppm to about 45 ppm, from about 5 ppm to about 40 ppm, from about 5 ppm to about 35 ppm, from about 5 ppm to about 30 ppm, from about 5 ppm to about 25 ppm, from about 5 ppm to about 20 ppm, from about 5 ppm to about 15 ppm, or from about 5 ppm to about 10 ppm. Alternatively, rebaudioside D2 can be present in consumable products of the present disclosure at a final concentration that ranges from about 5 ppm to about 100 ppm, from about 10 ppm to about 100 ppm, from about 15 ppm to about 100 ppm, from about 20 ppm to about 100 ppm, from about 25 ppm to about 100 ppm, from about 30 ppm to about 100 ppm, from about 35 ppm to about 100 ppm, from about 40 ppm to about 100 ppm, from about 45 ppm to about 100 ppm, from about 50 ppm to about 100 ppm, from about 55 ppm to about 100 ppm, from about 60 ppm to about 100 ppm, from about 65 ppm to about 100 ppm, from about 70 ppm to about 100 ppm, from about 75 ppm to about 100 ppm, from about 80 ppm to about 100 ppm, from about 85 ppm to about 100 ppm, from about 90 ppm to about 100 ppm, or from about 95 ppm to about 100 ppm.

In certain embodiments, from about 5 ppm to about 100 ppm of rebaudioside D2 is present in food product compositions. As used herein, "food product composition(s)" refers to any solid or liquid ingestible material that can, but need not, have a nutritional value and be intended for consumption by humans and animals.

Examples of suitable food product compositions can be, for example, confectionery compositions, such as candies, mints, fruit flavored drops, cocoa products, chocolates, and the like; condiments, such as ketchup, mustard, mayonnaise, and the like; chewing gums; cereal compositions; baked goods, such as breads, cakes, pies, cookies, and the like; dairy products, such as milk, cheese, cream, ice cream, sour cream, yogurt, sherbet, and the like; tabletop sweetener compositions; soups; stews; convenience foods; meats, such as ham, bacon, sausages, jerky, and the like; gelatins and gelatin-like products such as jams, jellies, preserves, and the like; fruits; vegetables; egg products; icings; syrups including molasses; snacks; nut meats and nut products; and animal feed.

Food product compositions can also be herbs, spices and seasonings, natural and synthetic flavors, and flavor enhancers, such as monosodium glutamate. In some embodiments, food product compositions can be, for example, prepared packaged products, such as dietetic sweeteners, liquid sweeteners, granulated flavor mixes, pet foods, livestock feed, tobacco, and materials for baking applications, such as powdered baking mixes for the preparation of breads, cookies, cakes, pancakes, donuts and the like. In other embodiments, food product compositions can also be diet and low-calorie food and beverages containing little or no sucrose.

In certain embodiments that may be combined with any of the preceding embodiments, the rebaudioside D2 is the only sweetener, and the product has a sweetness intensity equivalent to about 1% to about 4% (w/v-%) sucrose solution. In certain embodiments that can be combined with any of the preceding embodiments, the consumable products and beverage products can further include an additional sweetener, where the product has a sweetness intensity equivalent to about 1% to about 10% (w/v-%) sucrose solution. In certain embodiments that can be combined with any of the preceding embodiments, every sweetening ingredient in the product is a high intensity sweetener. In certain embodiments that can be combined with any of the preceding embodiments, every sweetening ingredient in the product can a natural high intensity sweetener. In certain embodiments that can be combined with any of the preceding embodiments, the additional sweetener contains one or more sweeteners selected from a *stevia* extract, a steviol glycoside, stevioside, rebaudioside A, rebaudioside B, rebaudioside C, rebaudioside D, rebaudioside F, dulcoside A, rubusoside, steviolbioside, sucrose, high fructose corn syrup, fructose, glucose, xylose, arabinose, rhamnose, erythritol, xylitol, mannitol, sorbitol, inositol, AceK, aspartame, neotame, sucralose, saccharine, naringin dihydrochalcone (NarDHC), neohesperidin dihydrochalcone (NDHC), rubusoside mogroside IV, siamenoside I, mogroside V, monatin, thaumatin, monellin, brazzein, L-alanine, glycine, Lo Han Guo, hernandulcin, phyllodulcin, trilobtain, and combinations thereof. In certain embodiments that can be combined with any of the preceding embodiments, the consumable products and beverage products can further include one or more additives selected from a carbohydrate, a polyol, an amino acid or salt thereof, a poly-amino acid or salt thereof, a sugar acid or salt thereof, a nucleotide, an organic acid, an inorganic acid, an organic salt, an organic acid salt, an organic base salt, an inorganic salt, a bitter compound, a flavorant, a flavoring ingredient, an astringent compound, a protein, a protein hydrolysate, a surfactant, an emulsifier, a flavonoids, an alcohol, a polymer, and combinations thereof. In certain embodiments that can be combined with any of the preceding embodiments, the rebaudioside D2 has a purity of about 50% to about 100% by weight before it is added into the product.

Sweetener

In another aspect, the present disclosure is directed to a sweetener consisting of a chemical structure:

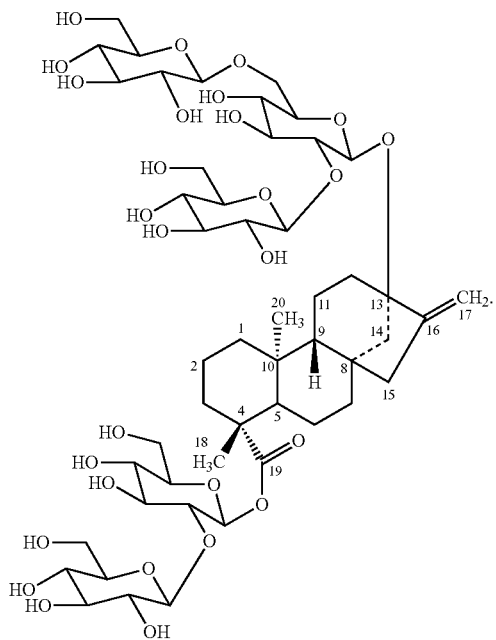

The sweetener can further include at least one of a filler, a bulking agent and an anticaking agent. Suitable fillers, bulking agents and anticaking agents are known in the art.

In certain embodiments, rebaudioside D2 sweetener can be included and/or added at a final concentration that is sufficient to sweeten and/or enhance the sweetness of the consumable products and beverage products. The "final concentration" of rebaudioside D2 refers to the concentration of rebaudioside D2 present in the final consumable products and beverage products (i.e., after all ingredients and/or compounds have been added to produce the consumable products and beverage products). Accordingly, in certain embodiments, rebaudioside D2 is included and/or added to a compound or ingredient used to prepare the consumable products and beverage products. The rebaudioside D2 may be present in a single compound or ingredient, or multiple compounds and ingredients. In other embodiments, rebaudioside D2 is included and/or added to the consumable products and beverage products. In certain preferred embodiments, the rebaudioside D2 is included and/or added at a final concentration that ranges from about 5 ppm to about 100 ppm, from about 5 ppm to about 95 ppm, from about 5 ppm to about 90 ppm, from about 5 ppm to about 85 ppm, from about 5 ppm to about 80 ppm, from about 5 ppm to about 75 ppm, from about 5 ppm to about 70 ppm, from about 5 ppm to about 65 ppm, from about 5 ppm to about 60 ppm, from about 5 ppm to about 55 ppm, from about 5 ppm to about 50 ppm, from about 5 ppm to about 45 ppm, from about 5 ppm to about 40 ppm, from about 5 ppm to about 35 ppm, from about 5 ppm to about 30 ppm, from about 5 ppm to about 25 ppm, from about 5 ppm to about 20 ppm, from about 5 ppm to about 15 ppm, or from about 5 ppm to about 10 ppm. Alternatively, the rebaudioside D2 is included and/or added at a final concentration that ranges from about 5 ppm to about 100 ppm, from about 10 ppm to about 100 ppm, from about 15 ppm to about 100 ppm, from about 20 ppm to about 100 ppm, from about 25 ppm to about 100 ppm, from about 30 ppm to about 100 ppm, from about 35 ppm to about 100 ppm, from about 40 ppm to about 100 ppm, from about 45 ppm to about 100 ppm, from about 50 ppm to about 100 ppm, from about 55 ppm to about 100 ppm, from about 60 ppm to about 100 ppm, from about 65 ppm to about 100 ppm, from about 70 ppm to about 100 ppm, from about 75 ppm to about 100 ppm, from about 80 ppm to about 100 ppm, from about 85 ppm to about 100 ppm, from about 90 ppm to about 100 ppm, or from about 95 ppm to about 100 ppm. For example, rebaudioside D2 may be included and/or added at a final concentration of about 5 ppm, about 10 ppm, about 15 ppm, about 20 ppm, about 25 ppm, about 30 ppm, about 35 ppm, about 40 ppm, about 45 ppm, about 50 ppm, about 55 ppm, about 60 ppm, about 65 ppm, about 70 ppm, about 75 ppm, about 80 ppm, about 85 ppm, about 90 ppm, about 95 ppm, or about 100 ppm, including any range in between these values.

In certain embodiments, rebaudioside D2 is the only sweetener included and/or added to the consumable products and the beverage products. In such embodiments, the consumable products and the beverage products have a sweetness intensity equivalent to about 1% to about 4% (w/v-%) sucrose solution, about 1% to about 3% (w/v-%) sucrose solution, or about 1% to about 2% (w/v-%) sucrose solution. Alternatively, the consumable products and the beverage products have a sweetness intensity equivalent to about 1% to about 4% (w/v-%) sucrose solution, about 2% to about 4% (w/v-%) sucrose solution, about 3% to about 4% (w/v-%) sucrose solution, or about 4%. For example, the consumable products and the beverage products may have a sweetness intensity equivalent to about 1%, about 2%, about 3%, or about 4% (w/v-%) sucrose solution, including any range in between these values.

The consumable products and beverage products of the present disclosure can include a mixture of rebaudioside D2 and one or more sweeteners of the present disclosure in a ratio sufficient to achieve a desirable sweetness intensity, nutritional characteristic, taste profile, mouthfeel, or other organoleptic factor.

The disclosure will be more fully understood upon consideration of the following non-limiting Examples.

EXAMPLES

Example 1

In this Example, full-length DNA fragments of all candidate UGT genes were synthesized.

Specifically, the cDNAs were codon optimized for *E. coli* expression (Genscript, Piscataway, N.J.). The synthesized DNA was cloned into a bacterial expression vector pETite N-His SUMO Kan Vector (Lucigen). For the nucleotide sequence encoding the UDP-glycosyltransferase fusion enzyme (EUS) (see, SEQ ID NO:6), a GSG-linker (encoded by the nucleotide sequence: ggttctggt) was inserted in frame between a nucleotide sequence encoding the *Oryze sativa* uridine diphospho glycosyltransferase (EUGT11) domain (see, SEQ ID NO:2) and the nucleotide sequence encoding the *A. thaliana* sucrose synthase 1 (AtSUS1) domain (see, SEQ ID NO:4). Table 2 summarizes the protein and sequence identifier numbers.

TABLE 2

Sequence Identification Numbers.

| Name | SEQ ID NO | Description |
| --- | --- | --- |
| EUGT11 | SEQ ID NO: 1 | Amino acid |
| EUGT11 | SEQ ID NO: 2 | Nucleic acid |
| AtSUS1 | SEQ ID NO: 3 | Amino acid |
| AtSUS1 | SEQ ID NO: 4 | Nucleic acid |
| EUS fusion enzyme | SEQ ID NO: 5 | Amino acid |
| EUS fusion enzyme | SEQ ID NO: 6 | Nucleic acid |

Each expression construct was transformed into *E. coli* BL21 (DE3), which was subsequently grown in LB media containing 50 μg/mL kanamycin at 37° C. until reaching an $OD_{600}$ of 0.8-1.0. Protein expression was induced by addition of 1 mM isopropyl β-D-1-thiogalactopyranoside (IPTG) and the culture was further grown at 16° C. for 22 hr. Cells were harvested by centrifugation (3,000×g; 10 min; 4° C.). The cell pellets were collected and were either used immediately or stored at −80° C.

Figure 2A:
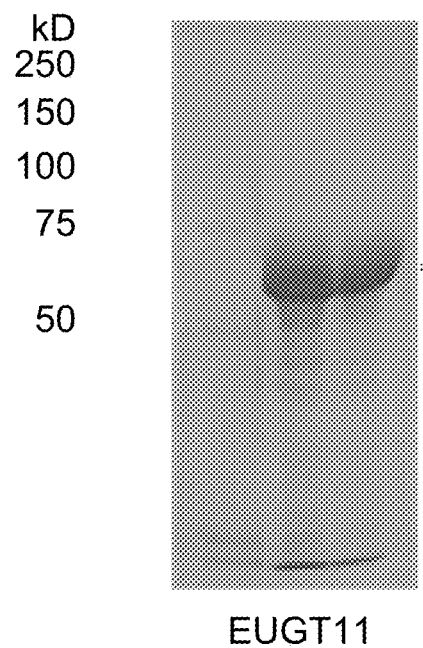
FIGS. 2A and 2B show the SDS-PAGE analysis of the purified recombinant UDP-glycosyltransferase enzyme (EUGT11) and the purified recombinant UDP-glycosyltransferase fusion enzyme (EUS), as discussed in Example 1.
Figure 2B:
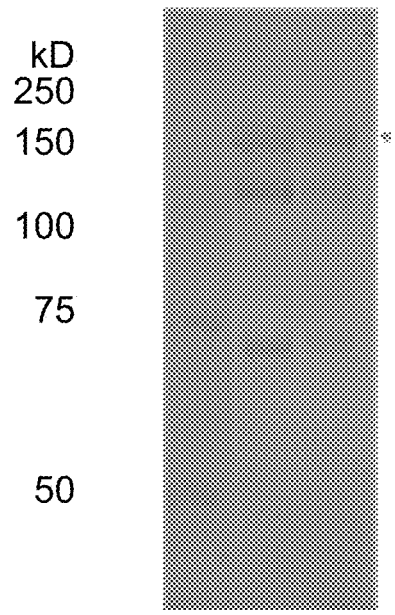

The cell pellets were re-suspended in lysis buffer (50 mM potassium phosphate buffer, pH 7.2, 25 μg/ml lysozyme, 5 μg/ml DNase I, 20 mM imidazole, 500 mM NaCl, 10% glycerol, and 0.4% TRITON X-100). The cells were disrupted by sonication at 4° C., and the cell debris was clarified by centrifugation (18,000×g; 30 min). The supernatant was loaded to a equilibrated (equilibration buffer: 50 mM potassium phosphate buffer, pH 7.2, 20 mM imidazole, 500 mM NaCl, 10% glycerol) Ni-NTA (Qiagen) affinity column. After loading of protein sample, the column was washed with equilibration buffer to remove unbound contaminant proteins. The His-tagged UGT recombinant polypeptides were eluted by equilibration buffer containing 250 mM imidazole. After purification, the recombinant EUGT11 protein (62 kD band indicated by arrow in FIG. 2A) and the EUS fusion enzyme (155 kD band indicated by arrow in FIG. 2B) were analyzed by SDS-PAGE. Molecular weight standards are indicated to left of each SDS-gel image.

Example 2

In this Example, recombinant EUGT11 protein and recombinant EUS fusion enzyme were assayed for 1,2-19 O-glucose glycosylation activity using rebaudioside A as the steviol glycoside substrate.

The recombinant polypeptides (10 μg) were tested in a 200 μL in vitro reaction system. The reaction system contained 50 mM potassium phosphate buffer, pH 7.2, 3 mM $MgCl_2$, 1 mg/ml steviol glycoside substrate, and 1 mM UDP-glucose. The reaction was performed at 30° C. and terminated by adding 200 μL of 1-butanol. The samples were extracted three times with 200 μL of 1-butanol. The pooled fraction was dried and dissolved in 70 μL of 80% methanol for high-performance liquid chromatography (HPLC) analysis. Rebaudioside A (purity 99%) was used as the substrate. Rebaudioside A was obtained from Blue California (Rancho Santa Margarita, Calif.). In vitro reactions were carried out for 14 hours and 24 hours. FIG. 3A shows the peak for rebaudioside D (labeled "Reb D") for comparison.

The UGT catalyzed glycosylation reaction was coupled to a UDP-glucose generating reaction (referred to herein as the "UGT-SUS coupling system") catalyzed by a sucrose synthase (e.g., AtSUS1). Specifically, the *Arabidopsis thaliana* sucrose synthase 1 (AtSUS1) sequence (Bieniawska et al., Plant J. 2007, 49: 810-828) was synthesized and inserted into a bacterial expression vector. The recombinant AtSUS1 protein was expressed and purified by affinity chromatography. The AtSUS1 protein was added to the EUGT11 protein to form an in vitro reaction mixture referred to herein as the EUGT11-AtSUS1 coupling system. In the resultant UGT-SUS (e.g., EUGT11-AtSUS1) coupling system, the UDP-glucose was generated from sucrose and UDP, such that the addition of an extra UDP-glucose was omitted.

HPLC analysis was performed using a Dionex UPLC ultimate 3000 system (Sunnyvale, Calif.), including a quaternary pump, a temperature controlled column compartment, an auto sampler and a UV absorbance detector. A Phenomenex Luna NH2 with guard column, 150×3.0 mm, 3 μm (100 A) was used for the characterization of steviol glycosides. 72% acetonitrile in water was used for isocratic elution in HPLC analysis.

As shown in FIG. 3, EUS and EUGT11 transferred a sugar moiety to rebaudioside A to produce rebaudioside D in all reaction conditions. Rebaudioside A was completely converted to rebaudioside D by the EUS fusion enzyme (FIGS. 3B and 3E) and the UGT-SUS (i.e., EUGT11-AtSUS1) coupling reaction system (FIGS. 5D and 5G) at incubation times of 14 hours and 24 hours. However, rebaudioside A was only partially converted to rebaudioside D at 14 hours (FIG. 3C) and 24 hours (FIG. 3F) by the EUGT11 enzyme alone. Furthermore, the same molecule amount of EUS had a higher enzymatic activity than the EUGT11 and converted all of the rebaudioside A to rebaudioside D at incubation times of 14 hours (FIG. 3B) and 24 hours (FIG. 3E). These results demonstrated that the reaction of the UGT-SUS (i.e., EUGT11-AtSUS1) coupling system could be achieved using the EUS fusion enzyme. Additionally, these results demonstrated that EUGT11 showed a 1,2-19 O-glucose glycosylation activity to produce rebaudioside D from rebaudioside A (FIGS. 3C and 3F) and that AtSUS1 enhanced the conversion efficiency by EUGT11 in the UGT-SUS coupling system (FIGS. 3B, 3D, 3E and 3G). FIG. 3A shows peaks for stevioside (labeled "Ste"), rebaudioside A (labeled "Reb A") and rebaudioside D (labeled "Reb D") for comparison.

Example 3

In this Example, EUGT11 and EUS were assayed for 1,2-19 O-glucose glycosylation activity using stevioside as the steviol glycoside substrate at incubation times of 14 hours and 24 hours as described in Example 2.

In addition to the conversion of rebaudioside A to rebaudioside D by EUGT11 as discussed in Example 2 above, EUGT11 also converted stevioside to rebaudioside E (labeled "Reb E" in FIG. 4). Surprisingly, an unexpected compound, rebaudioside D2 (labelled "Reb D2" in FIG. 4), having a HPLC retention time of about 7.28 minutes was produced by both EUGT11 and EUS in all reactions. When AtSUS1 was added to the EUGT11 reaction mixture to create the UGT-SUS coupling system (FIGS. 4D and 4G) and when EUS was used (FIGS. 4B and 4E), more rebaudioside D2 was produced. Along with the increase in rebaudioside D2 production, rebaudioside E (labeled "Reb E" in FIGS. 4C and 4F) that was produced was consumed during the production of the rebaudioside D2. These results indicated that EUGT11 can catalyze the reaction to produce a rebaudioside (rebaudioside D2) from rebaudioside E. FIG. 4A shows peaks for stevioside (labeled "Ste"), rebaudioside A (labeled "Reb A") and rebaudioside D (labeled "Reb D") for comparison.

Example 4

In this Example, to confirm the conversion of rebaudioside E to rebaudioside D2 in vitro, EUGT11 and EUS were assayed using rebaudioside E as the steviol glycoside substrate as described in Example 2.

Figure 5A:
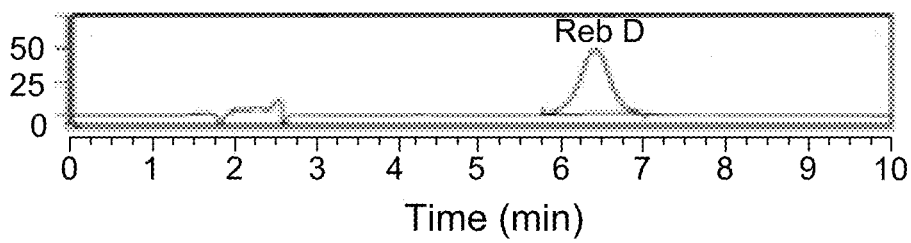
FIGS. 5A-5J are graphs showing the HPLC retention times of rebaudioside D ("Reb-D") standard (FIG. 5A); rebaudioside E ("Reb-E") standard (FIG. 5B); rebaudioside D2 ("Reb D2") enzymatically produced by EUGT11 at 12 hours (FIG. 5C); the UGT-SUS (EUGT11-SUS1) coupling system at 12 hours (FIG. 5D) and EUS at 12 hours (FIG. 5E); rebaudioside D ("Reb D") enzymatically produced by a UGT76G1-AtSUS1 coupling system at 12 hours (FIG. 5F); rebaudioside D2 enzymatically produced by EUGT11 at 24 hours (FIG. 5G); rebaudioside D2 enzymatically produced by UGT-SUS (EUGT11-SUS1) coupling system at 24 hours (FIG. 5H); rebaudioside D2 enzymatically produced by EUS at 24 hours (FIG. 5I); and rebaudioside D enzymatically produced by a UGT76G1-AtSUS1 coupling system at 24 hours (FIG. 5J), as discussed in Example 4.
Figure 5B:
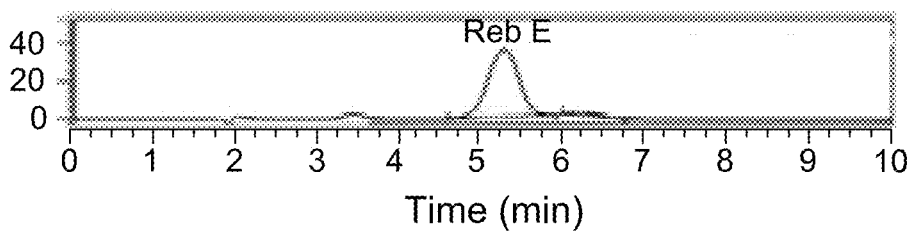

For comparison, the enzymatic activities of another UGT (UGT76G1) was also assayed. UGT76G1, from *stevia*, has been identified as an enzyme that transfers a sugar residue to C-3' of the C13 O-glucose of stevioside to form rebaudioside A. As shown in FIGS. 5F and 5J, when UGT76G1 was used in the UGT-SUS coupling system, a sugar residue was transferred to the C-3' of the C13 O-glucose of rebaudioside E to form rebaudioside D. FIGS. 5A and 5B show purified rebaudioside D ("Reb D") and rebaudioside E ("Reb-E") for comparison.

Figure 5C:
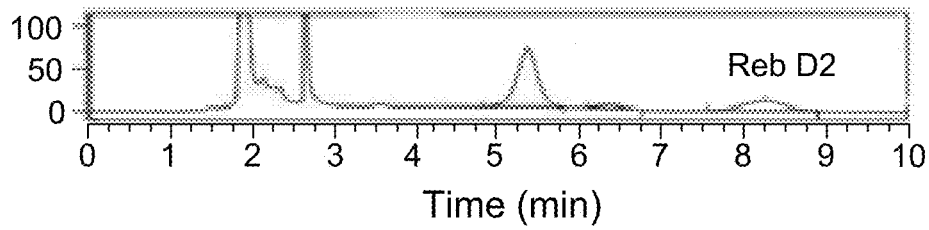
Figure 5D:
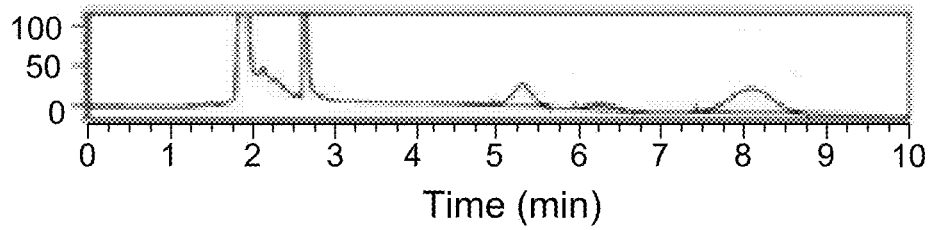
Figure 5E:
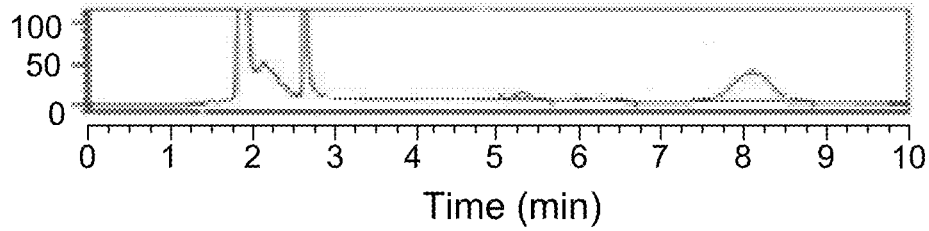
Figure 5F:
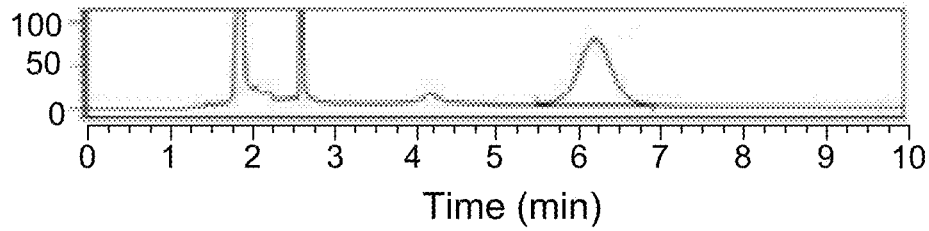
Figure 5G:
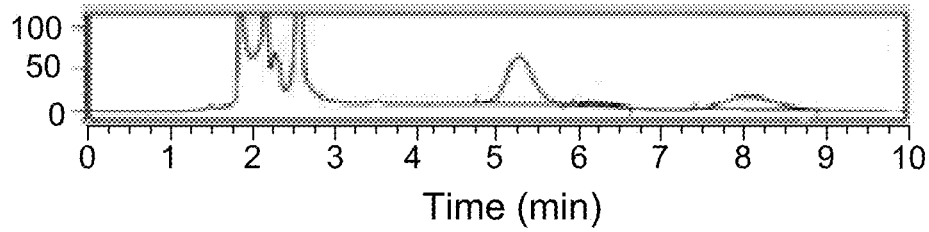
Figure 5H:
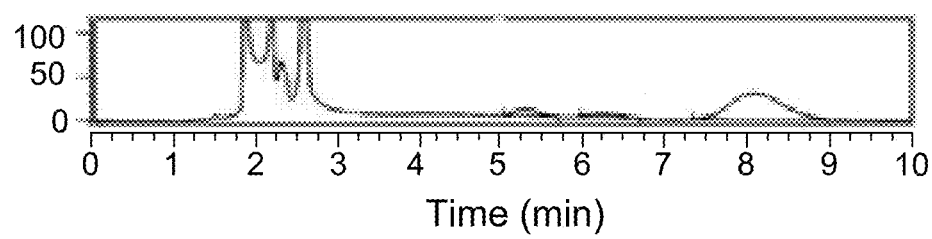
Figure 5I:
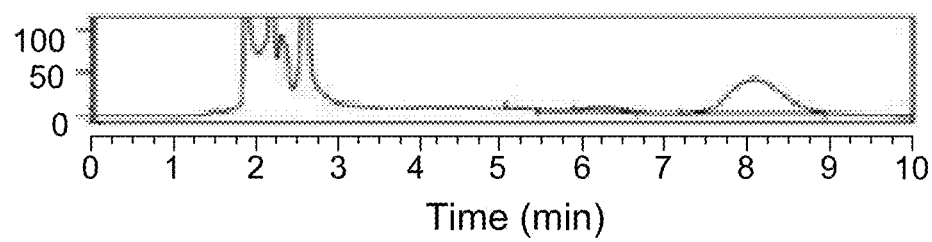
Figure 5J:
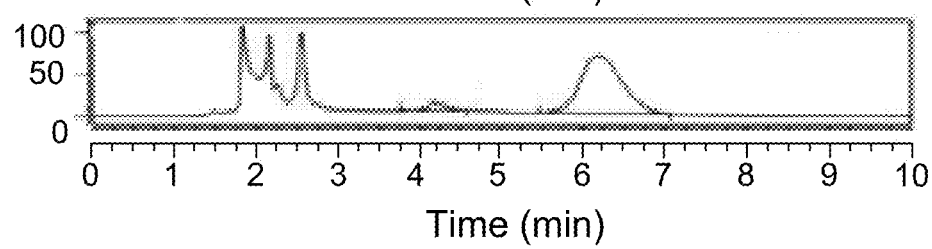

As discussed in Example 3 above and shown in FIGS. 5C and 5G, EUGT11 alone could transfer one glucose molecule to rebaudioside E to form a rebaudioside (referred to herein as "rebaudioside D2" and labeled "Reb D2" in FIGS. 5C and 5G) that was distinct from rebaudiosides D and E (compare peaks in FIG. 5A and FIG. 5B, respectively). EUGT11 in the UGT-SUS coupling system (FIGS. 5D and 5H) and EUS (FIGS. 5E and 5I) enhanced the conversion from rebaudioside E to rebaudioside D2.

These results demonstrated that EUGT11 is a UGT with 1,2-19 O-glucose glycosylation activity to produce related steviol glycosides. EUGT11 can catalyze the reaction to produce Reb-E from stevioside as substrate and Reb D from Reb A as substrate. Surprisingly, a compound (Reb D2) was unexpectedly synthesized in the in vitro reaction with stevioside as substrate. Further experiments confirmed that Reb D2 was directly synthesized from Reb E. According to the structure of Reb D2, in the in vitro reaction, EUGT11 transferred a D-glucose to the C-6' of the C13 O-glucose of Reb-E to generate a 1,6-β-glycosidic linkage.

Example 5

In this Example, the rebaudioside (rebaudioside D2) was purified from an enlarged in vitro reaction and prepared for liquid chromatography/mass spectrometry (LC/MS) and nuclear magnetic resonance (NMR) analysis.

The rebaudioside (rebaudioside D2) was purified from an enlarged in vitro reaction. The in vitro reaction was monitored by HPLC analysis. At the desired time point, Reb D2 compound was purified by column and concentrated by vacuum drying. The purified Reb D2 was white powder with 95% purity. The collected Reb D2 compound was used for High Resolution Mass Spectra (HRMS) analysis. HRMS data were generated with a LTQ Orbitrap Discovery HRMS instrument, with its resolution set to 30 k and data was scanned from m/z 150 to 1500 in positive ion electrospray mode. The needle voltage was set to 4 kV; the other source conditions were sheath gas=25, aux gas=0, sweep gas=5 (all gas flows in arbitrary units), capillary voltage=30V, capillary temperature=300° C., and tube lens voltage=75. The sample was diluted with 2:2:1 acetonitrile:methanol:water (same as infusion eluent) and 50 microliters of sample were injected. Nuclear Magnetic Resonance (NMR) spectra were acquired using a Bruker Avance DRX 500 MHz instrument or a Varian INOVA 600 MHz instrument using standard pulse sequences. The 1D ($^1$H and $^{13}$C) and 2D (TOCSY, HMQC, and HMBC) NMR spectra were performed in pyridine-d5 (also known as $C_5D_5N$).

The molecular formula of Reb D2 was deduced as $C_{50}H_{80}O_{28}$ on the basis of its positive high resolution mass spectrum (HRMS) which showed adduct ions corresponding to $[M+NH_4]^+$ and $[M+Na]^+$ at m/z 1146.5169 and 1151.4721 respectively; this composition was supported by the $^{13}$C NMR spectral data. The $^1$H NMR spectral data of Reb D2 showed the presence of two methyl singlets at δ 1.10 and 1.44, two olefinic protons as singlets at δ 5.09 and 5.72 of an exocyclic double bond, nine sp3 methylene and two sp3 methine protons between δ 0.74-2.80, which is characteristic for the ent-kaurane diterpenoids isolated from the genus *Stevia*.

The basic skeleton of ent-kaurane diterpenoids was supported by the TOCSY studies which showed key correlations: H-1/H-2; H-2/H-3; H-5/H-6; H-6/H-7; H-9/H-11; H-11/H-12. The $^1$H NMR spectrum of Reb D2 also showed the presence of anomeric protons resonating at δ 5.04, 5.10, 5.21, 5.48, and 6.30; suggesting five sugar units in its structure. Acid hydrolysis of Reb D2 with 5% $H_2SO_4$ afforded D-glucose which was identified by direct comparison with an authentic sample by TLC. The large coupling constants observed for the five anomeric protons of the glucose moieties at δ 5.04 (d, J=7.5 Hz), 5.10 (d, J=7.4 Hz), 5.21 (d, J=7.9 Hz), 5.48 (d, J=7.9 Hz), and 6.30 (d, J=7.9 Hz), suggested their β-orientation as reported for other steviol glycosides. The $^1$H and $^{13}$C NMR values for Reb D2 were assigned on the basis of TOCSY, HMQC and HMBC data and are summarized in Table 3.

TABLE 3

$^1$H and $^{13}$C NMR values for Reb D2 and Reb E.

| | Reb D2 (1) | | Reb E(2) | |
|---|---|---|---|---|
| Position | $^1$H NMR | $^{13}$C NMR | $^1$H NMR | $^{13}$C NMR |
| 1 | 0.74 t (12.8), 1.67 m | 41.2 | 0.73 t (13.3), 1.68 m | 41 |
| 2 | 1.48 m, 2.12 m | 20.6 | 1.46 m, 2.13 m | 20.6 |
| 3 | 1.13 m, 2.80 d (12.8) | 38.4 | 1.12 m, 2.78 d (12.8) | 38.2 |

TABLE 3-continued

¹H and ¹³C NMR values for Reb D2 and Reb E.

| Position | Reb D2 (1) ¹H NMR | Reb D2 (1) ¹³C NMR | Reb E(2) ¹H NMR | Reb E(2) ¹³C NMR |
|---|---|---|---|---|
| 4 | — | 44.9 | — | 44.8 |
| 5 | 0.98 d (11.8) | 58.1 | 0.97 d (11.8) | 38.2 |
| 6 | 1.87 m, 2.10 m | 22.6 | 1.85 m, 2.09 m | 22.6 |
| 7 | 1.28 m, 1.64 m | 42.2 | 1.27 m, 1.63 m | 42.1 |
| 8 | — | 43.3 | — | 43 |
| 9 | 0.88 d, (7.5) | 54.5 | 0.88 br s | 54.5 |
| 10 | — | 40.3 | — | 40.2 |
| 11 | 1.66 m | 21.2 | 1.65 m | 21.1 |
| 12 | 1.91 m, 2.22 m | 38.2 | 1.96 m, 2.16 m | 37.8 |
| 13 | — | 86.8 | — | 86.6 |
| 14 | 1.69 d, (11.4), 2.49 d, (11.0) | 44.9 | 1.74 d, (11.4), 2.54 d, (11.0) | 44.8 |
| 15 | 2.04 m, 2.16 m | 48.6 | 2.04 m, 2.12 m | 48.5 |
| 16 | — | 155 | — | 154.9 |
| 17 | 5.09 s, 5.72 s | 105.4 | 5.09 s, 5.76 s | 105.4 |
| 18 | 1.44 s | 29.9 | 1.43 s | 29.8 |
| 19 | — | 176.3 | — | 176.2 |
| 20 | 1.10 s | 17.3 | 1.10 s | 17.2 |
| 1' | 6.30 d (7.9) | 93.9 | 6.30 d (7.9) | 93.9 |
| 2' | 4.38 m | 81.5 | 4.38 m | 81.7 |
| 3' | 4.27 m | 78.5 | 4.26 m | 78.4 |
| 4' | 4.24 m | 72 | 4.22 m | 72.1 |
| 5' | 3.94 m | 79.6 | 3.92 m | 79.5 |
| 6' | 4.33 m, 4.43 m | 62.7 | 4.33 m, 4.43 m | 62.6 |
| 1" | 5.10 d (7.4) | 98.3 | 5.16 d (7.5) | 98.4 |
| 2" | 4.18 m | 84.8 | 4.17 m | 84.9 |
| 3" | 4.29 m | 78.6 | 4.32 m | 78.5 |
| 4" | 4.20 m | 71.3 | 4.22 m | 71.8 |
| 5" | 3.78 m | 78.5 | 3.72 m | 78.2 |
| 6" | 4.32 m, 4.57 m | 69.8 | 4.26 m, 4.35 m | 62.9 |
| 1''' | 5.21 d (7.9) | 107.2 | 5.32 d (7.5) | 107.2 |
| 2''' | 4.14 t (8.4) | 77.6 | 4.15 t (8.4) | 77.7 |
| 3''' | 4.25 m | 78.7 | 4.26 m | 78.6 |
| 4''' | 4.34 m | 72.4 | 4.36 m | 72.3 |
| 5''' | 3.94 m | 79.1 | 3.96 m | 79 |
| 6''' | 4.43 m, 4.53 m | 63.3 | 4.46 m, 4.56 m | 63.2 |
| 1'''' | 5.48 d (7.9) | 106.2 | 5.48 d (7.9) | 106.2 |
| 2'''' | 4.04 t (7.9) | 76.8 | 4.06 t (7.9) | 76.8 |
| 3'''' | 4.22 m | 78.8 | 4.25 m | 78.7 |
| 4'''' | 4.32 m | 71.2 | 4.31 m | 71.2 |
| 5'''' | 3.99 m | 79.1 | 4.02 m | 79.1 |
| 6'''' | 4.38 m, 4.55 m | 63.5 | 4.42 m, 4.54 m | 63.4 |
| 1''''' | 5.04 d (7.5) | 105.9 | | |
| 2''''' | 4.02 m | 77 | | |
| 3''''' | 4.21 m | 78.6 | | |
| 4''''' | 4.25 m | 72.2 | | |
| 5''''' | 3.96 m | 79.1 | | |
| 6''''' | 4.34 m, 4.48 m | 63.3 | | |

Based on the extensive 1D (¹H and ¹³C), 2D NMR (TOCSY, HMQC, and HMBC) and high resolution mass spectral (HRMS) data, the structure of Reb D2 was identified and compared to the structure of rebaudioside E (see, FIG. 6).

Figure 7:
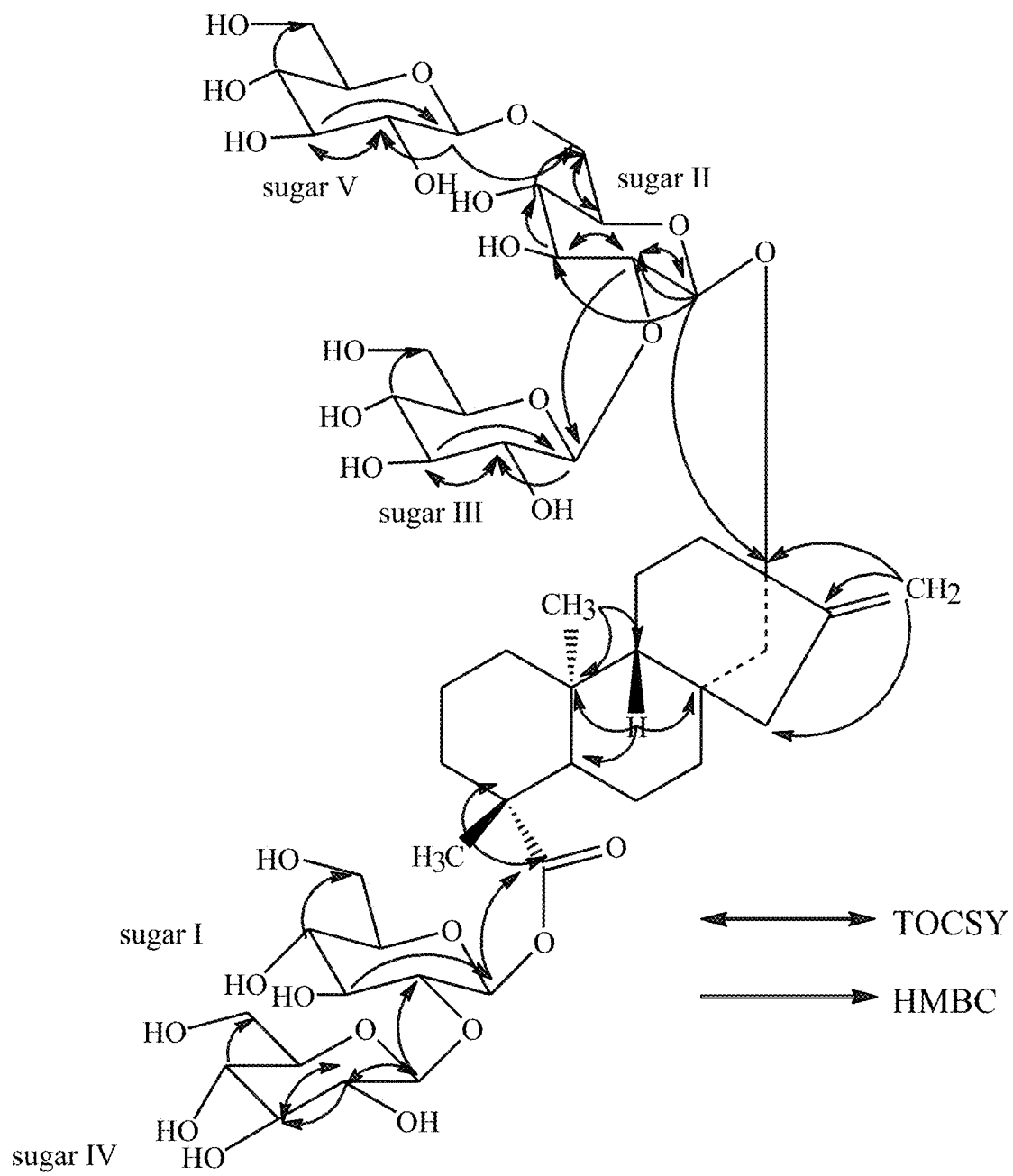
FIG. 7 is a chemical structure of rebaudioside D2 illustrating the key TOCSY and HMBC correlations, as discussed in Example 5.

Based on the results from NMR spectral data and hydrolysis experiments of Reb D2, it was concluded that there were five β-D-glucosyl units in its structure connected to the aglycone steviol. A close comparison of the ¹H and ¹³C NMR values of Reb D2 with rebaudioside E (see, Table 2) suggested the presence of a steviol aglycone moiety with a 2-O-β-D-glucobiosyl unit at C13 in the form of an ether linkage and another 2-O-β-D-glucobiosyl unit at C19 position in the form of an ester linkage, leaving the assignment of the additional β-D-glucosyl unit. Further, from the ¹³C NMR spectral data of Reb D2 which showed that one of the five oxymethine carbons of sugar moieties appeared downfield at δ 69.8, suggested the placement of the additional β-D-glucosyl unit at this position. Identical proton and carbon spectral data for the two sugars I and IV in Reb D2 and Reb E suggested the placement of the additional β-D-glucosyl unit at the 6-position of either sugar II or sugar III. The downfield shift for both the ¹H and ¹³C chemical shifts at the 6-position of sugar II of the β-D-glucosyl moiety suggested the additional β-D-glucosyl unit was attached at this position. The structure was further supported by the key TOCSY and HMBC correlations as shown in FIG. 7.

Based on the results of NMR and mass spectral data as well as hydrolysis studies, the structure of Reb D2 produced by the enzymatic conversion of rebaudioside E was deduced as 13-[(2-O-β-D-glucopyranosyl-6-O-β-D-glucopyranosyl-β-D-glucopyranosyl)oxy] ent-kaur-16-en-19-oic acid-(2-O-β-D-glucopyranosyl-β-D-glucopyranosyl) ester.

13-[(2-O-β-D-glucopyranosyl-6-O-β-D-glucopyranosyl-β-D-glucopyranosyl)oxy] ent-kaur-16-en-19-oic acid-(2-O-β-D-glucopyranosyl-β-D-glucopyranosyl) Ester (Reb D2)

White powder; ¹H-NMR (600 MHz, C₅D₅N, δ ppm) and ¹³C-NMR (150 MHz, C₅D₅N, δ ppm) spectroscopic data see Table 2; HRMS (M+NH₄)⁺ m/z 1146.5169 (calcd. for C₅₀H₈₄O₂₈N: 1146.5180), (M+Na)⁺ m/z 1151.4721 (calcd. for C₅₀H₈₀O₂₈Na: 1151.4734).

To a solution of Reb D2 (5 mg) in MeOH (10 ml) was added 3 ml of 5% H₂SO₄ and the mixture was refluxed for 24 hours. The reaction mixture was then neutralized with saturated sodium carbonate and extracted with ethyl acetate (EtOAc) (2×25 ml) to give an aqueous fraction containing sugars and an EtOAc fraction containing the aglycone part. The aqueous phase was concentrated and compared with standard sugars using the TLC systems EtOAc/n-butanol/water (2:7:1) and CH₂Cl₂/MeOH/water (10:6:1); the sugar was identified as D-glucose.

The structure of Reb D2 was confirmed as 13-[(2-O-β-D-glucopyranosyl-6-O-β-D-glucopyranosyl-β-D-glucopyranosyl)oxy] ent-kaur-16-en-19-oic acid-(2-O-β-D-glucopyranosyl-β-D-glucopyranosyl) ester on the basis of extensive 1D (¹H and ¹³C), and 2D NMR (TOCSY, HMQC, and HMBC), as well as high resolution mass spectral data and hydrolysis studies.

Example 6

In this Example, the structure of the rebaudioside (rebaudioside D2) was compared to Reb-E and Reb-D.

According to the steviol glycosides database, only Reb-D contains five β-D-glucosyl units in its structure connected to the aglycone steviol, two glycosidic residues at the C19 position and three glycosidic residues at the C13 position of the aglycone steviol. UGT76G1 from *stevia* has been identified as an enzyme that transfers a sugar residue to C-3' of the C13 O-glucose of Reb E to form rebaudioside D (see, FIGS. 5F and 5J). Reb D2 is a steviol glycoside that also contains five D-glycosidic residues with different structure comparison to rebaudioside D (see, FIG. 8). The fifth glycosidic residue ("sugar V") of rebaudioside D2 is positioned at the C-6' of the C-13-O glucose of Reb E by a 1,6 β glycosidic linkage, whereas the fifth glycosidic residue ("sugar V") of rebaudioside D is positioned at the C-3' of the C13 O-glucose of Reb E by a 1,3 β glycosidic linkage (see, FIG. 8). As described herein, both EUGT11 and EUG can directly convert Reb E into Reb D2 in vitro.

Example 7

In this Example, a taste test was conducted on Reb D2.

Sensory evaluation of Reb D2 was performed using sucrose as a control. The sucrose sample purchased from Sigma-Aldrich and prepared control samples at three different concentrations of 1.0%, 3.0%, and 6.0% sucrose in bottled water (w/v) at room temperature. The steviol glycoside Reb D2 at 300, and 600 ppm for sensory evaluation was prepared by adding corresponding mass into a 1000 mL of bottled water. The mixture was stirred at room temperature and the steviol glycoside sample was then evaluated against several control sucrose samples at 1.0%, 3.0%, and 6.0% by a panel of nine volunteers.

The blind results showed consistent results among majority of nine volunteers at two different concentrations (300 and 600 ppm) of the Reb D2; the overall % sweetness equivalence (SE) averages were about 2.4 and 5.4, respectively. The result indicates that the rebaudioside D2 is about 80-90 times sweeter to sucrose.

Example 8

In this Example, the solubility of Reb D2 was compared to Reb D.

Reb D2 and Reb D were added to water to prepare solutions with 0.25 mM, 0.5 mM, 1 mM, 1.5 mM, 2 mM, 5 mM and 10 mM Reb D2 and Reb D. Reb D2 powder completely dissolved in water immediately, however only 0.25 mM Reb D totally dissolved in water. Additionally, solutions of Reb D at concentrations of 0.5 mM, 1 mM, 1.5 mM, 2 mM, 5 mM and 10 mM did not dissolve when heated at 30° C. for 72 hours.

These results demonstrate that Reb D2 has a higher solubility in water than does Reb D.

In view of the above, it will be seen that the several advantages of the disclosure are achieved and other advantageous results attained. As various changes could be made in the above methods and systems without departing from the scope of the disclosure, it is intended that all matter contained in the above description and shown in the accompanying drawings shall be interpreted as illustrative and not in a limiting sense.

When introducing elements of the present disclosure or the various versions, embodiment(s) or aspects thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A method for synthesizing rebaudioside E, the method comprising:
preparing a reaction mixture comprising stevioside; a substrate selected from the group consisting of sucrose, uridine diphosphate (UDP) and uridine diphosphate-glucose (UDP-glucose); and a UDP-glycosyltransferase fusion enzyme comprising a uridine diphospho glycosyltransferase domain coupled to a sucrose synthase domain, wherein the uridine diphospho glycosyltransferase domain is an *Oryza sativa* uridine diphospho glycosyltransferase EUGT11 comprising the amino acid sequence of SEQ ID NO: 1, and the sucrose synthase domain is selected from the group consisting of an *Arabidopsis* sucrose synthase 1, a *Coffea* sucrose synthase 1, and a *Stevia* sucrose synthase 1, and wherein the UDP-glycosyltransferase fusion enzyme covalently couples a glucose to the stevioside to produce rebaudioside E.

2. The method of claim 1, wherein the UDP-glycosyltransferase fusion enzyme comprises an amino acid sequence having about 90% sequence identity to SEQ ID NO:5.

3. The method of claim 1, wherein the sucrose synthase domain is an *Arabidopsis thaliana* sucrose synthase 1.

4. The method of claim 3, wherein the sucrose synthase domain comprises the amino acid sequence of SEQ ID NO:3.

5. The method of claim 1, wherein the UDP-glycosyltransferase fusion enzyme is expressed in a host organism.

6. The method of claim 5, wherein the host organism is a bacterial cell.

7. The method of claim 5, wherein the host organism is a yeast cell.

8. The method of claim 5, wherein the host organism is an *E. coli* cell.

9. The method of claim 2, wherein the UDP-glycosyltransferase fusion enzyme comprises an amino acid sequence having about 95% sequence identity to SEQ ID NO: 5.

10. The method of claim 9, wherein the UDP-glycosyltransferase fusion enzyme comprises the amino acid sequence of SEQ ID NO: 5.

* * * * *

SEQUENCE LISTING

```
<160> NUMBER OF SEQ ID NOS: 6

<210> SEQ ID NO 1
<211> LENGTH: 462
<212> TYPE: PRT
<213> ORGANISM: Artificial Sequence
<220> FEATURE:
<223> OTHER INFORMATION: Synthetic

<400> SEQUENCE: 1

Met Asp Ser Gly Tyr Ser Ser Ser Tyr Ala Ala Ala Ala Gly Met His
1               5                   10                  15

Val Val Ile Cys Pro Trp Leu Ala Phe Gly His Leu Leu Pro Cys Leu
            20                  25                  30

Asp Leu Ala Gln Arg Leu Ala Ser Arg Gly His Arg Val Ser Phe Val
        35                  40                  45

Ser Thr Pro Arg Asn Ile Ser Arg Leu Pro Pro Val Arg Pro Ala Leu
    50                  55                  60

Ala Pro Leu Val Ala Phe Val Ala Leu Pro Leu Pro Arg Val Glu Gly
65                  70                  75                  80

Leu Pro Asp Gly Ala Glu Ser Thr Asn Asp Val Pro His Asp Arg Pro
                85                  90                  95

Asp Met Val Glu Leu His Arg Arg Ala Phe Asp Gly Leu Ala Ala Pro
            100                 105                 110

Phe Ser Glu Phe Leu Gly Thr Ala Cys Ala Asp Trp Val Ile Val Asp
        115                 120                 125

Val Phe His His Trp Ala Ala Ala Ala Ala Leu Glu His Lys Val Pro
```

```
                130               135               140
Cys Ala Met Met Leu Leu Gly Ser Ala His Met Ile Ala Ser Ile Ala
145                 150               155                 160

Asp Arg Arg Leu Glu Arg Ala Glu Thr Glu Ser Pro Ala Ala Ala Gly
                165                 170                 175

Gln Gly Arg Pro Ala Ala Pro Thr Phe Glu Val Ala Arg Met Lys
            180                 185                 190

Leu Ile Arg Thr Lys Gly Ser Ser Gly Met Ser Leu Ala Glu Arg Phe
                195                 200                 205

Ser Leu Thr Leu Ser Arg Ser Ser Leu Val Val Gly Arg Ser Cys Val
    210                 215                 220

Glu Phe Glu Pro Glu Thr Val Pro Leu Leu Ser Thr Leu Arg Gly Lys
225                 230                 235                 240

Pro Ile Thr Phe Leu Gly Leu Met Pro Pro Leu His Glu Gly Arg Arg
                245                 250                 255

Glu Asp Gly Glu Asp Ala Thr Val Arg Trp Leu Asp Ala Gln Pro Ala
                260                 265                 270

Lys Ser Val Val Tyr Val Ala Leu Gly Ser Glu Val Pro Leu Gly Val
            275                 280                 285

Glu Lys Val His Glu Leu Ala Leu Gly Leu Glu Leu Ala Gly Thr Arg
        290                 295                 300

Phe Leu Trp Ala Leu Arg Lys Pro Thr Gly Val Ser Asp Ala Asp Leu
305                 310                 315                 320

Leu Pro Ala Gly Phe Glu Glu Arg Thr Arg Gly Arg Gly Val Val Ala
                325                 330                 335

Thr Arg Trp Val Pro Gln Met Ser Ile Leu Ala His Ala Ala Val Gly
                340                 345                 350

Ala Phe Leu Thr His Cys Gly Trp Asn Ser Thr Ile Glu Gly Leu Met
            355                 360                 365

Phe Gly His Pro Leu Ile Met Leu Pro Ile Phe Gly Asp Gln Gly Pro
        370                 375                 380

Asn Ala Arg Leu Ile Glu Ala Lys Asn Ala Gly Leu Gln Val Ala Arg
385                 390                 395                 400

Asn Asp Gly Asp Gly Ser Phe Asp Arg Glu Gly Val Ala Ala Ile
                405                 410                 415

Arg Ala Val Ala Val Glu Glu Ser Ser Lys Val Phe Gln Ala Lys
                420                 425                 430

Ala Lys Lys Leu Gln Glu Ile Val Ala Asp Met Ala Cys His Glu Arg
            435                 440                 445

Tyr Ile Asp Gly Phe Ile Gln Gln Leu Arg Ser Tyr Lys Asp
450                 455                 460

<210> SEQ ID NO 2
<211> LENGTH: 1389
<212> TYPE: DNA
<213> ORGANISM: Artificial Sequence
<220> FEATURE:
<223> OTHER INFORMATION: Synthetic

<400> SEQUENCE: 2
atggattcgg gttactcttc ctcctatgcg gcggctgcgg gtatgcacgt tgttatctgt    60
ccgtggctgg cttttggtca cctgctgccg tgcctggatc tggcacagcg tctggcttca   120
cgcggccatc gtgtcagctt cgtgtctacc ccgcgcaata tttcgcgtct gccgccggtt   180
cgtccggcac tggctccgct ggttgcattt gtcgctctgc cgctgccgcg cgtggaaggt   240
```

```
ctgccggatg gtgcggaaag taccaacgac gtgccgcatg atcgcccgga catggttgaa      300
ctgcaccgtc gtgcattcga tggtctggca gcaccgtttt ccgaatttct gggtacggcg      360
tgcgccgatt gggtgatcgt tgacgtcttt catcactggg cggcggcggc ggcgctggaa      420
cataaagttc cgtgtgcaat gatgctgctg gctcagctc acatgattgc gtcgatcgca       480
gaccgtcgcc tggaacgtgc agaaaccgaa agtccggctg cggccggcca gggtcgcccg      540
gcagctgcgc cgaccttcga agtggcccgc atgaaactga ttcgtacgaa aggcagctct      600
ggtatgagcc tggcagaacg ctttagtctg accctgtccc gtagttccct ggtggttggt      660
cgcagttgcg ttgaatttga accggaaacc gtcccgctgc tgtccacgct gcgtggtaaa      720
ccgatcacct ttctgggtct gatgccgccg ctgcatgaag ccgtcgcga agatggtgaa       780
gacgcaacgg tgcgttggct ggatgcacag ccggctaaaa gcgtcgtgta tgtcgccctg      840
ggctctgaag tgccgctggg tgtggaaaaa gttcacgaac tggcactggg cctggaactg      900
gctggcaccc gcttcctgtg gcactgcgt aaaccgacgg gtgtgagcga tgcggacctg       960
ctgccggccg ttttgaaga acgtacccgc ggccgtggtg ttgtcgcaac gcgttgggtc      1020
ccgcaaatga gcattctggc gcatgccgca gtgggcgcct ttctgaccca ctgtggttgg      1080
aacagcacga tcgaaggcct gatgtttggt cacccgctga ttatgctgcc gatcttcggc      1140
gatcagggtc cgaacgcacg tctgattgaa gcgaaaaatg ccggcctgca agttgcgcgc      1200
aacgatggcg acggttcttt cgaccgtgag ggtgtggctg cggccattcg cgcagtggct      1260
gttgaagaag aatcatcgaa agttttcag gcgaaagcca aaaaactgca agaaatcgtc      1320
gcggatatgg cctgccacga acgctacatt gatggtttca ttcagcaact gcgctcctac      1380
aaagactaa                                                              1389
```

<210> SEQ ID NO 3
<211> LENGTH: 808
<212> TYPE: PRT
<213> ORGANISM: Artificial Sequence
<220> FEATURE:
<223> OTHER INFORMATION: Synthetic

<400> SEQUENCE: 3

```
Met Ala Asn Ala Glu Arg Met Ile Thr Arg Val His Ser Gln Arg Glu
1               5                   10                  15

Arg Leu Asn Glu Thr Leu Val Ser Glu Arg Asn Glu Val Leu Ala Leu
            20                  25                  30

Leu Ser Arg Val Glu Ala Lys Gly Lys Gly Ile Leu Gln Gln Asn Gln
        35                  40                  45

Ile Ile Ala Glu Phe Glu Ala Leu Pro Glu Gln Thr Arg Lys Lys Leu
    50                  55                  60

Glu Gly Gly Pro Phe Phe Asp Leu Leu Lys Ser Thr Gln Glu Ala Ile
65                  70                  75                  80

Val Leu Pro Pro Trp Val Ala Leu Ala Val Arg Pro Arg Pro Gly Val
                85                  90                  95

Trp Glu Tyr Leu Arg Val Asn Leu His Ala Leu Val Val Glu Glu Leu
            100                 105                 110

Gln Pro Ala Glu Phe Leu His Phe Lys Glu Glu Leu Val Asp Gly Val
        115                 120                 125

Lys Asn Gly Asn Phe Thr Leu Glu Leu Asp Phe Glu Pro Phe Asn Ala
    130                 135                 140

Ser Ile Pro Arg Pro Thr Leu His Lys Tyr Ile Gly Asn Gly Val Asp
```

-continued

```
            145                 150                 155                 160
        Phe Leu Asn Arg His Leu Ser Ala Lys Leu Phe His Asp Lys Glu Ser
                        165                 170                 175
        Leu Leu Pro Leu Leu Lys Phe Leu Arg Leu His Ser His Gln Gly Lys
                        180                 185                 190
        Asn Leu Met Leu Ser Glu Lys Ile Gln Asn Leu Asn Thr Leu Gln His
                        195                 200                 205
        Thr Leu Arg Lys Ala Glu Glu Tyr Leu Ala Glu Leu Lys Ser Glu Thr
            210                 215                 220
        Leu Tyr Glu Glu Phe Glu Ala Lys Phe Glu Glu Ile Gly Leu Glu Arg
        225                 230                 235                 240
        Gly Trp Gly Asp Asn Ala Glu Arg Val Leu Asp Met Ile Arg Leu Leu
                        245                 250                 255
        Leu Asp Leu Leu Glu Ala Pro Asp Pro Cys Thr Leu Glu Thr Phe Leu
                        260                 265                 270
        Gly Arg Val Pro Met Val Phe Asn Val Val Ile Leu Ser Pro His Gly
                        275                 280                 285
        Tyr Phe Ala Gln Asp Asn Val Leu Gly Tyr Pro Asp Thr Gly Gly Gln
                        290                 295                 300
        Val Val Tyr Ile Leu Asp Gln Val Arg Ala Leu Glu Ile Glu Met Leu
        305                 310                 315                 320
        Gln Arg Ile Lys Gln Gln Gly Leu Asn Ile Lys Pro Arg Ile Leu Ile
                        325                 330                 335
        Leu Thr Arg Leu Leu Pro Asp Ala Val Gly Thr Thr Cys Gly Glu Arg
                        340                 345                 350
        Leu Glu Arg Val Tyr Asp Ser Glu Tyr Cys Asp Ile Leu Arg Val Pro
                        355                 360                 365
        Phe Arg Thr Glu Lys Gly Ile Val Arg Lys Trp Ile Ser Arg Phe Glu
                        370                 375                 380
        Val Trp Pro Tyr Leu Glu Thr Tyr Thr Glu Asp Ala Ala Val Glu Leu
        385                 390                 395                 400
        Ser Lys Glu Leu Asn Gly Lys Pro Asp Leu Ile Ile Gly Asn Tyr Ser
                        405                 410                 415
        Asp Gly Asn Leu Val Ala Ser Leu Leu Ala His Lys Leu Gly Val Thr
                        420                 425                 430
        Gln Cys Thr Ile Ala His Ala Leu Glu Lys Thr Lys Tyr Pro Asp Ser
                        435                 440                 445
        Asp Ile Tyr Trp Lys Lys Leu Asp Asp Lys Tyr His Phe Ser Cys Gln
            450                 455                 460
        Phe Thr Ala Asp Ile Phe Ala Met Asn His Thr Asp Phe Ile Ile Thr
        465                 470                 475                 480
        Ser Thr Phe Gln Glu Ile Ala Gly Ser Lys Glu Thr Val Gly Gln Tyr
                        485                 490                 495
        Glu Ser His Thr Ala Phe Thr Leu Pro Gly Leu Tyr Arg Val Val His
                        500                 505                 510
        Gly Ile Asp Val Phe Asp Pro Lys Phe Asn Ile Val Ser Pro Gly Ala
                        515                 520                 525
        Asp Met Ser Ile Tyr Phe Pro Tyr Thr Glu Glu Lys Arg Arg Leu Thr
            530                 535                 540
        Lys Phe His Ser Glu Ile Glu Glu Leu Leu Tyr Ser Asp Val Glu Asn
        545                 550                 555                 560
        Lys Glu His Leu Cys Val Leu Lys Asp Lys Lys Pro Ile Leu Phe
                        565                 570                 575
```

```
Thr Met Ala Arg Leu Asp Arg Val Lys Asn Leu Ser Gly Leu Val Glu
            580                 585                 590
Trp Tyr Gly Lys Asn Thr Arg Leu Arg Glu Leu Ala Asn Leu Val Val
        595                 600                 605
Val Gly Gly Asp Arg Arg Lys Glu Ser Lys Asp Asn Glu Glu Lys Ala
610                 615                 620
Glu Met Lys Lys Met Tyr Asp Leu Ile Glu Glu Tyr Lys Leu Asn Gly
625                 630                 635                 640
Gln Phe Arg Trp Ile Ser Ser Gln Met Asp Arg Val Arg Asn Gly Glu
                645                 650                 655
Leu Tyr Arg Tyr Ile Cys Asp Thr Lys Gly Ala Phe Val Gln Pro Ala
            660                 665                 670
Leu Tyr Glu Ala Phe Gly Leu Thr Val Val Glu Ala Met Thr Cys Gly
        675                 680                 685
Leu Pro Thr Phe Ala Thr Cys Lys Gly Gly Pro Ala Glu Ile Ile Val
690                 695                 700
His Gly Lys Ser Gly Phe His Ile Asp Pro Tyr His Gly Asp Gln Ala
705                 710                 715                 720
Ala Asp Thr Leu Ala Asp Phe Phe Thr Lys Cys Lys Glu Asp Pro Ser
                725                 730                 735
His Trp Asp Glu Ile Ser Lys Gly Gly Leu Gln Arg Ile Glu Glu Lys
            740                 745                 750
Tyr Thr Trp Gln Ile Tyr Ser Gln Arg Leu Leu Thr Leu Thr Gly Val
        755                 760                 765
Tyr Gly Phe Trp Lys His Val Ser Asn Leu Asp Arg Leu Glu Ala Arg
770                 775                 780
Arg Tyr Leu Glu Met Phe Tyr Ala Leu Lys Tyr Arg Pro Leu Ala Gln
785                 790                 795                 800
Ala Val Pro Leu Ala Gln Asp Asp
                805
```

<210> SEQ ID NO 4
<211> LENGTH: 2427
<212> TYPE: DNA
<213> ORGANISM: Artificial Sequence
<220> FEATURE:
<223> OTHER INFORMATION: Synthetic

<400> SEQUENCE: 4

| | | | | |
|---|---|---|---|---|
| atggcaaacg | ctgaacgtat | gataacgcgc | gtccacagcc | aacgtgagcg | tttgaacgaa | 60 |
| acgcttgttt | ctgagagaaa | cgaagtcctt | gccttgcttt | ccagggttga | agccaaaggt | 120 |
| aaaggtattt | tacaacaaaa | ccagatcatt | gctgaattcg | aagctttgcc | tgaacaaacc | 180 |
| cggaagaaac | ttgaaggtgg | tcctttcttt | gaccttctca | aatccactca | ggaagcaatt | 240 |
| gtgttgccac | catgggttgc | tctagctgtg | aggccaaggc | ctggtgtttg | gaatactta | 300 |
| cgagtcaatc | tccatgctct | tgtcgttgaa | gaactccaac | tgctgagtt | tcttcatttc | 360 |
| aaggaagaac | tcgttgatgg | agttaagaat | ggtaatttca | ctcttgagct | tgatttcgag | 420 |
| ccattcaatg | cgtctatccc | tcgtccaaca | ctccacaaat | acattggaaa | tggtgttgac | 480 |
| ttccttaacc | gtcatttatc | ggctaagctc | ttccatgaca | aggagagttt | gcttccattg | 540 |
| cttaagttcc | ttcgtcttca | cagccaccag | ggcaagaacc | tgatgttgag | cgagaagatt | 600 |
| cagaacctca | cactctgca | acacaccttg | aggaaagcag | aagagtatct | agcagagctt | 660 |
| aagtccgaaa | cactgtatga | agagtttgag | gccaagtttg | aggagattgg | tcttgagagg | 720 |

-continued

```
ggatggggag acaatgcaga gcgtgtcctt gacatgatac gtcttctttt ggaccttctt     780
gaggcgcctg atccttgcac tcttgagact tttcttggaa gagtaccaat ggtgttcaac     840
gttgtgatcc tctctccaca tggttacttt gctcaggaca atgttcttgg ttaccctgac     900
actggtggac aggttgttta cattcttgat caagttcgtg ctctggagat agagatgctt     960
caacgtatta agcaacaagg actcaacatt aaaccaagga ttctcattct aactcgactt    1020
ctacctgatg cggtaggaac tacatgcggt gaacgtctcg agagagttta tgattctgag    1080
tactgtgata tcttcgtgt gcccttcaga acagagaagg gtattgttcg caaatggatc    1140
tcaaggttcg aagtctggcc atatctagag acttacaccg aggatgctgc ggttgagcta    1200
tcgaaagaat tgaatggcaa gcctgacctt atcattggta actacagtga tggaaatctt    1260
gttgcttctt tattggctca caaacttggt gtcactcagt gtaccattgc tcatgctctt    1320
gagaaaacaa agtacccgga ttctgatatc tactggaaga gcttgacga caagtaccat    1380
ttctcatgcc agtcactgc ggatattttc gcaatgaacc acactgattt catcatcact    1440
agtactttcc aagaaattgc tggaagcaaa gaaactgttg ggcagtatga agccacaca    1500
gccttactc ttcccggatt gtatcgagtt gttcacggga ttgatgtgtt tgatcccaag    1560
ttcaacattg tctctcctgg tgctgatatg agcatctact tcccttacac agaggagaag    1620
cgtagattga ctaagttcca ctctgagatc gaggagctcc tctacagcga tgttgagaac    1680
aaagagcact tatgtgtgct caaggacaag aagaagccga ttctcttcac aatggctagg    1740
cttgatcgtg tcaagaactt gtcaggtctt gttgagtggt acgggaagaa caccgcttg    1800
cgtgagctag ctaacttggt tgttgttgga ggagacagga ggaaagagtc aaaggacaat    1860
gaagagaaag cagagatgaa gaaaatgtat gatctcattg aggaatacaa gctaaacggt    1920
cagttcaggt ggatctcctc tcagatggac cgggtaagga acggtgagct gtaccggtac    1980
atctgtgaca ccaagggtgc ttttgtccaa cctgcattat atgaagcctt tgggttaact    2040
gttgtggagg ctatgacttg tggtttaccg actttcgcca cttgcaaagg tggtccagct    2100
gagatcattg tgcacggtaa atcgggttc cacattgacc cttaccatgg tgatcaggct    2160
gctgatactc ttgctgattt cttcaccaag tgtaaggagg atccatctca ctgggatgag    2220
atctcaaaag gagggcttca gaggattgag gagaaataca cttggcaaat ctattcacag    2280
aggctcttga cattgactgg tgtgtatgga ttctggaagc atgtctcgaa ccttgaccgt    2340
cttgaggctc gccgttacct tgaaatgttc tatgcattga agtatcgccc attggctcag    2400
gctgttcctc ttgcacaaga tgattga                                        2427
```

<210> SEQ ID NO 5
<211> LENGTH: 1272
<212> TYPE: PRT
<213> ORGANISM: Artificial Sequence
<220> FEATURE:
<223> OTHER INFORMATION: Synthetic

<400> SEQUENCE: 5

```
Met Asp Ser Gly Tyr Ser Ser Tyr Ala Ala Ala Gly Met His
1               5                   10                  15

Val Val Ile Cys Pro Trp Leu Ala Phe Gly His Leu Leu Pro Cys Leu
                20                  25                  30

Asp Leu Ala Gln Arg Leu Ala Ser Arg Gly His Arg Val Ser Phe Val
            35                  40                  45

Ser Thr Pro Arg Asn Ile Ser Arg Leu Pro Pro Val Arg Pro Ala Leu
```

```
                50                  55                  60
Ala Pro Leu Val Ala Phe Val Ala Leu Pro Leu Pro Arg Val Glu Gly
 65                  70                  75                  80

Leu Pro Asp Gly Ala Glu Ser Thr Asn Asp Val Pro His Asp Arg Pro
                 85                  90                  95

Asp Met Val Glu Leu His Arg Arg Ala Phe Asp Gly Leu Ala Ala Pro
            100                 105                 110

Phe Ser Glu Phe Leu Gly Thr Ala Cys Ala Asp Trp Val Ile Val Asp
            115                 120                 125

Val Phe His His Trp Ala Ala Ala Ala Leu Glu His Lys Val Pro
130                 135                 140

Cys Ala Met Met Leu Leu Gly Ser Ala His Met Ile Ala Ser Ile Ala
145                 150                 155                 160

Asp Arg Arg Leu Glu Arg Ala Glu Thr Glu Ser Pro Ala Ala Gly
            165                 170                 175

Gln Gly Arg Pro Ala Ala Ala Pro Thr Phe Glu Val Ala Arg Met Lys
            180                 185                 190

Leu Ile Arg Thr Lys Gly Ser Ser Gly Met Ser Leu Ala Glu Arg Phe
            195                 200                 205

Ser Leu Thr Leu Ser Arg Ser Ser Leu Val Val Gly Arg Ser Cys Val
210                 215                 220

Glu Phe Glu Pro Glu Thr Val Pro Leu Leu Ser Thr Leu Arg Gly Lys
225                 230                 235                 240

Pro Ile Thr Phe Leu Gly Leu Met Pro Pro Leu His Glu Gly Arg Arg
            245                 250                 255

Glu Asp Gly Glu Asp Ala Thr Val Arg Trp Leu Asp Ala Gln Pro Ala
            260                 265                 270

Lys Ser Val Val Tyr Val Ala Leu Gly Ser Glu Val Pro Leu Gly Val
            275                 280                 285

Glu Lys Val His Glu Leu Ala Leu Gly Leu Glu Leu Ala Gly Thr Arg
            290                 295                 300

Phe Leu Trp Ala Leu Arg Lys Pro Thr Gly Val Ser Asp Ala Asp Leu
305                 310                 315                 320

Leu Pro Ala Gly Phe Glu Glu Arg Thr Arg Gly Arg Gly Val Val Ala
            325                 330                 335

Thr Arg Trp Val Pro Gln Met Ser Ile Leu Ala His Ala Ala Val Gly
            340                 345                 350

Ala Phe Leu Thr His Cys Gly Trp Asn Ser Thr Ile Glu Gly Leu Met
            355                 360                 365

Phe Gly His Pro Leu Ile Met Leu Pro Ile Phe Gly Asp Gln Gly Pro
            370                 375                 380

Asn Ala Arg Leu Ile Glu Ala Lys Asn Ala Gly Leu Gln Val Ala Arg
385                 390                 395                 400

Asn Asp Gly Asp Gly Ser Phe Asp Arg Glu Gly Val Ala Ala Ala Ile
            405                 410                 415

Arg Ala Val Ala Val Glu Glu Glu Ser Ser Lys Val Phe Gln Ala Lys
            420                 425                 430

Ala Lys Lys Leu Gln Glu Ile Val Ala Asp Met Ala Cys His Glu Arg
            435                 440                 445

Tyr Ile Asp Gly Phe Ile Gln Gln Leu Arg Ser Tyr Lys Asp Gly Ser
            450                 455                 460

Gly Ala Asn Ala Glu Arg Met Ile Thr Arg Val His Ser Gln Arg Glu
465                 470                 475                 480
```

```
Arg Leu Asn Glu Thr Leu Val Ser Glu Arg Asn Val Leu Ala Leu
                485                 490                 495

Leu Ser Arg Val Glu Ala Lys Gly Lys Gly Ile Leu Gln Gln Asn Gln
            500                 505                 510

Ile Ile Ala Glu Phe Glu Ala Leu Pro Glu Gln Thr Arg Lys Lys Leu
        515                 520                 525

Glu Gly Gly Pro Phe Phe Asp Leu Leu Lys Ser Thr Gln Glu Ala Ile
    530                 535                 540

Val Leu Pro Pro Trp Val Ala Leu Ala Val Arg Pro Arg Pro Gly Val
545                 550                 555                 560

Trp Glu Tyr Leu Arg Val Asn Leu His Ala Leu Val Val Glu Glu Leu
                565                 570                 575

Gln Pro Ala Glu Phe Leu His Phe Lys Glu Glu Leu Val Asp Gly Val
            580                 585                 590

Lys Asn Gly Asn Phe Thr Leu Glu Leu Asp Phe Glu Pro Phe Asn Ala
        595                 600                 605

Ser Ile Pro Arg Pro Thr Leu His Lys Tyr Ile Gly Asn Gly Val Asp
    610                 615                 620

Phe Leu Asn Arg His Leu Ser Ala Lys Leu Phe His Asp Lys Glu Ser
625                 630                 635                 640

Leu Leu Pro Leu Leu Lys Phe Leu Arg Leu His Ser His Gln Gly Lys
                645                 650                 655

Asn Leu Met Leu Ser Glu Lys Ile Gln Asn Leu Asn Thr Leu Gln His
            660                 665                 670

Thr Leu Arg Lys Ala Glu Glu Tyr Leu Ala Glu Leu Lys Ser Glu Thr
        675                 680                 685

Leu Tyr Glu Glu Phe Glu Ala Lys Phe Glu Glu Ile Gly Leu Glu Arg
    690                 695                 700

Gly Trp Gly Asp Asn Ala Glu Arg Val Leu Asp Met Ile Arg Leu Leu
705                 710                 715                 720

Leu Asp Leu Leu Glu Ala Pro Asp Pro Cys Thr Leu Glu Thr Phe Leu
                725                 730                 735

Gly Arg Val Pro Met Val Phe Asn Val Val Ile Leu Ser Pro His Gly
            740                 745                 750

Tyr Phe Ala Gln Asp Asn Val Leu Gly Tyr Pro Asp Thr Gly Gly Gln
        755                 760                 765

Val Val Tyr Ile Leu Asp Gln Val Arg Ala Leu Glu Ile Glu Met Leu
    770                 775                 780

Gln Arg Ile Lys Gln Gln Gly Leu Asn Ile Lys Pro Arg Ile Leu Ile
785                 790                 795                 800

Leu Thr Arg Leu Leu Pro Asp Ala Val Gly Thr Thr Cys Gly Glu Arg
                805                 810                 815

Leu Glu Arg Val Tyr Asp Ser Glu Tyr Cys Asp Ile Leu Arg Val Pro
            820                 825                 830

Phe Arg Thr Glu Lys Gly Ile Val Arg Lys Trp Ile Ser Arg Phe Glu
        835                 840                 845

Val Trp Pro Tyr Leu Glu Thr Tyr Thr Glu Asp Ala Ala Val Glu Leu
    850                 855                 860

Ser Lys Glu Leu Asn Gly Lys Pro Asp Leu Ile Ile Gly Asn Tyr Ser
865                 870                 875                 880

Asp Gly Asn Leu Val Ala Ser Leu Leu Ala His Lys Leu Gly Val Thr
                885                 890                 895
```

Gln Cys Thr Ile Ala His Ala Leu Glu Lys Thr Lys Tyr Pro Asp Ser
            900                 905                 910

Asp Ile Tyr Trp Lys Lys Leu Asp Asp Lys Tyr His Phe Ser Cys Gln
        915                 920                 925

Phe Thr Ala Asp Ile Phe Ala Met Asn His Thr Asp Phe Ile Ile Thr
    930                 935                 940

Ser Thr Phe Gln Glu Ile Ala Gly Ser Lys Glu Thr Val Gly Gln Tyr
945                 950                 955                 960

Glu Ser His Thr Ala Phe Thr Leu Pro Gly Leu Tyr Arg Val Val His
                965                 970                 975

Gly Ile Asp Val Phe Asp Pro Lys Phe Asn Ile Val Ser Pro Gly Ala
            980                 985                 990

Asp Met Ser Ile Tyr Phe Pro Tyr Thr Glu Glu Lys Arg Arg Leu Thr
        995                 1000                1005

Lys Phe His Ser Glu Ile Glu Glu Leu Leu Tyr Ser Asp Val Glu
    1010                1015                1020

Asn Lys Glu His Leu Cys Val Leu Lys Asp Lys Lys Pro Ile
    1025                1030                1035

Leu Phe Thr Met Ala Arg Leu Asp Arg Val Lys Asn Leu Ser Gly
    1040                1045                1050

Leu Val Glu Trp Tyr Gly Lys Asn Thr Arg Leu Arg Glu Leu Ala
    1055                1060                1065

Asn Leu Val Val Val Gly Gly Asp Arg Arg Lys Glu Ser Lys Asp
    1070                1075                1080

Asn Glu Glu Lys Ala Glu Met Lys Lys Met Tyr Asp Leu Ile Glu
    1085                1090                1095

Glu Tyr Lys Leu Asn Gly Gln Phe Arg Trp Ile Ser Ser Gln Met
    1100                1105                1110

Asp Arg Val Arg Asn Gly Glu Leu Tyr Arg Tyr Ile Cys Asp Thr
    1115                1120                1125

Lys Gly Ala Phe Val Gln Pro Ala Leu Tyr Glu Ala Phe Gly Leu
    1130                1135                1140

Thr Val Val Glu Ala Met Thr Cys Gly Leu Pro Thr Phe Ala Thr
    1145                1150                1155

Cys Lys Gly Gly Pro Ala Glu Ile Ile Val His Gly Lys Ser Gly
    1160                1165                1170

Phe His Ile Asp Pro Tyr His Gly Asp Gln Ala Ala Asp Thr Leu
    1175                1180                1185

Ala Asp Phe Phe Thr Lys Cys Lys Glu Asp Pro Ser His Trp Asp
    1190                1195                1200

Glu Ile Ser Lys Gly Gly Leu Gln Arg Ile Glu Glu Lys Tyr Thr
    1205                1210                1215

Trp Gln Ile Tyr Ser Gln Arg Leu Leu Thr Leu Thr Gly Val Tyr
    1220                1225                1230

Gly Phe Trp Lys His Val Ser Asn Leu Asp Arg Leu Glu Ala Arg
    1235                1240                1245

Arg Tyr Leu Glu Met Phe Tyr Ala Leu Lys Tyr Arg Pro Leu Ala
    1250                1255                1260

Gln Ala Val Pro Leu Ala Gln Asp Asp
    1265                1270

<210> SEQ ID NO 6
<211> LENGTH: 3819
<212> TYPE: DNA

<213> ORGANISM: Artificial Sequence
<220> FEATURE:
<223> OTHER INFORMATION: Synthetic

<400> SEQUENCE: 6

| | | | | | |
|---|---|---|---|---|---|
| atggattcgg | gttactcttc | ctcctatgcg | gcggctgcgg | gtatgcacgt | tgttatctgt | 60 |
| ccgtggctgg | cttttggtca | cctgctgccg | tgcctggatc | tggcacagcg | tctggcttca | 120 |
| cgcggccatc | gtgtcagctt | cgtgtctacc | ccgcgcaata | tttcgcgtct | gccgccggtt | 180 |
| cgtccggcac | tggctccgct | ggttgcattt | gtcgctctgc | cgctgccgcg | cgtggaaggt | 240 |
| ctgccggatg | gtgcggaaag | taccaacgac | gtgccgcatg | atcgcccgga | catggttgaa | 300 |
| ctgcaccgtc | gtgcattcga | tggtctggca | gcaccgtttt | ccgaatttct | gggtacggcg | 360 |
| tgcgccgatt | gggtgatcgt | tgacgtcttt | catcactggg | cggcggcggc | ggcgctggaa | 420 |
| cataaagttc | cgtgtgcaat | gatgctgctg | ggctcagctc | acatgattgc | gtcgatcgca | 480 |
| gaccgtcgcc | tggaacgtgc | agaaaccgaa | agtccggctg | cggccggcca | gggtcgcccg | 540 |
| gcagctgcgc | cgaccttcga | agtggcccgc | atgaaactga | ttcgtacgaa | aggcagctct | 600 |
| ggtatgagcc | tggcagaacg | ctttagtctg | accctgtccc | gtagttccct | ggtggttggt | 660 |
| cgcagttgcg | ttgaatttga | accggaaacc | gtcccgctgc | tgtccacgct | gcgtggtaaa | 720 |
| ccgatcacct | ttctgggtct | gatgccgccg | ctgcatgaag | ccgtcgcga | agatggtgaa | 780 |
| gacgcaacg | tgcgttggct | ggatgcacag | ccggctaaaa | gcgtcgtgta | tgtcgccctg | 840 |
| ggctctgaag | tgccgctggg | tgtggaaaaa | gttcacgaac | tggcactggg | cctggaactg | 900 |
| gctggcaccc | gcttcctgtg | ggcactgcgt | aaaccgacgg | tgtgagcga | tgcggacctg | 960 |
| ctgccggccg | gttttgaaga | acgtacccgc | ggccgtggtg | ttgtcgcaac | gcgttgggtc | 1020 |
| ccgcaaatga | gcattctggc | gcatgccgca | gtgggcgcct | ttctgaccca | ctgtggttgg | 1080 |
| aacagcacga | tcgaaggcct | gatgtttggt | cacccgctga | ttatgctgcc | gatcttcggc | 1140 |
| gatcagggtc | cgaacgcacg | tctgattgaa | gcgaaaaatg | ccggcctgca | agttgcgcgc | 1200 |
| aacgatggcg | acggttcttt | cgaccgtgag | ggtgtggctg | cggccattcg | cgcagtggct | 1260 |
| gttgaagaag | aatcatcgaa | agtttttcag | gcgaaagcca | aaaaactgca | agaaatcgtc | 1320 |
| gcggatatgg | cctgccacga | acgctacatt | gatggtttca | ttcagcaact | gcgctcctac | 1380 |
| aaagacggtt | ctggtgcaaa | cgctgaacgt | atgataacgc | gcgtccacag | ccaacgtgag | 1440 |
| cgtttgaacg | aaacgcttgt | ttctgagaga | aacgaagtcc | ttgccttgct | ttccagggtt | 1500 |
| gaagccaaag | gtaaaggtat | tttacaacaa | aaccagatca | ttgctgaatt | cgaagctttg | 1560 |
| cctgaacaaa | cccggaagaa | acttgaaggt | ggtcctttct | ttgaccttct | caaatccact | 1620 |
| caggaagcaa | ttgtgttgcc | accatggggt | gctctagctg | tgaggccaag | gcctggtgtt | 1680 |
| tgggaatact | tacgagtcaa | tctccatgct | cttgtcgttg | aagaactcca | acctgctgag | 1740 |
| tttcttcatt | tcaaggaaga | actcgttgat | ggagttaaga | atggtaattt | cactcttgag | 1800 |
| cttgatttcg | agccattcaa | tgcgtctatc | cctcgtccaa | cactccacaa | atacattgga | 1860 |
| aatggtgttg | acttccttaa | ccgtcattta | tcggctaagc | tcttccatga | caaggagagt | 1920 |
| ttgcttccat | tgcttaagtt | ccttcgtctt | cacagccacc | agggcaagaa | cctgatgttg | 1980 |
| agcgagaaga | ttcagaacct | caacactctg | caacacacct | tgaggaaagc | agaagagtat | 2040 |
| ctagcagagc | ttaagtccga | aacactgtat | gaagagtttg | aggccaagtt | tgaggagatt | 2100 |
| ggtcttgaga | ggggatgggg | agacaatgca | gagcgtgtcc | ttgacatgat | acgtcttctt | 2160 |
| ttggaccttc | ttgaggcgcc | tgatccttgc | actcttgaga | cttttcttgg | aagagtacca | 2220 |

```
atggtgttca acgttgtgat cctctctcca catggttact ttgctcagga caatgttctt  2280
ggttaccctg acactggtgg acaggttgtt tacattcttg atcaagttcg tgctctggag  2340
atagagatgc ttcaacgtat taagcaacaa ggactcaaca ttaaaccaag gattctcatt  2400
ctaactcgac ttctacctga tgcggtagga actacatgcg gtgaacgtct cgagagagtt  2460
tatgattctg agtactgtga tattcttcgt gtgcccttca gaacagagaa gggtattgtt  2520
cgcaaatgga tctcaaggtt cgaagtctgg ccatatctag agacttacac cgaggatgct  2580
gcggttgagc tatcgaaaga attgaatggc aagcctgacc ttatcattgg taactacagt  2640
gatgaaaatc ttgttgcttc tttattggct cacaaacttg gtgtcactca gtgtaccatt  2700
gctcatgctc ttgagaaaac aaagtacccg gattctgata tctactggaa gaagcttgac  2760
gacaagtacc atttctcatg ccagttcact gcggatattt tcgcaatgaa ccacactgat  2820
ttcatcatca ctagtacttt ccaagaaatt gctggaagca agaaactgt tgggcagtat  2880
gaaagccaca cagcctttac tcttcccgga ttgtatcgag ttgttcacgg gattgatgtg  2940
tttgatccca agttcaacat tgtctctcct ggtgctgata tgagcatcta cttcccttac  3000
acagaggaga agcgtagatt gactaagttc cactctgaga tcgaggagct cctctacagc  3060
gatgttgaga acaaagagca cttatgtgtg ctcaaggaca agaagaagcc gattctcttc  3120
acaatggcta ggcttgatcg tgtcaagaac ttgtcaggtc ttgttgagtg gtacgggaag  3180
aacacccgct tgcgtgagct agctaacttg gttgttgttg gaggagacag gaggaaagag  3240
tcaaaggaca atgaagagaa agcagagatg aagaaaatgt atgatctcat tgaggaatac  3300
aagctaaacg gtcagttcag gtggatctcc tctcagatgg accgggtaag gaacggtgag  3360
ctgtaccggt acatctgtga caccaagggt gcttttgtcc aacctgcatt atatgaagcc  3420
tttgggttaa ctgttgtgga ggctatgact tgtggtttac cgactttcgc cacttgcaaa  3480
ggtggtccag ctgagatcat tgtgcacggt aaatcgggtt tccacattga cccttaccat  3540
ggtgatcagg ctgctgatac tcttgctgat ttcttcacca agtgtaagga ggatccatct  3600
cactgggatg agatctcaaa aggagggctt cagaggattg aggagaaata cacttggcaa  3660
atctattcac agaggctctt gacattgact ggtgtgtatg gattctggaa gcatgtctcg  3720
aaccttgacc gtcttgaggc tcgccgttac cttgaaatgt tctatgcatt gaagtatcgc  3780
ccattggctc aggctgttcc tcttgcacaa gatgattga                         3819
```